United States Patent
Steenackers et al.

(10) Patent No.: US 10,151,975 B2
(45) Date of Patent: Dec. 11, 2018

(54) LITHOGRAPHIC PRINTING PLATE PRECURSOR

(71) Applicant: AGFA NV, Mortsel (BE)

(72) Inventors: Marin Steenackers, Mortsel (BE); Johan Loccufier, Mortsel (BE); Sam Verbrugghe, Mortsel (BE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 15/037,332

(22) PCT Filed: Dec. 10, 2014

(86) PCT No.: PCT/EP2014/077175
§ 371 (c)(1),
(2) Date: May 18, 2016

(87) PCT Pub. No.: WO2015/086659
PCT Pub. Date: Jun. 18, 2015

(65) Prior Publication Data
US 2016/0282718 A1    Sep. 29, 2016

(30) Foreign Application Priority Data
Dec. 11, 2013   (EP) .................... 13196658

(51) Int. Cl.
| G03F 7/32 | (2006.01) |
| G03F 7/027 | (2006.01) |
| B41C 1/10 | (2006.01) |
| C07C 233/18 | (2006.01) |
| G03F 7/031 | (2006.01) |
| G03F 7/30 | (2006.01) |
| G03F 7/20 | (2006.01) |
| G03F 7/004 | (2006.01) |

(52) U.S. Cl.
CPC ............... G03F 7/027 (2013.01); B41C 1/10 (2013.01); B41C 1/1008 (2013.01); C07C 233/18 (2013.01); G03F 7/031 (2013.01); G03F 7/20 (2013.01); G03F 7/30 (2013.01); B41C 2210/04 (2013.01); B41C 2210/06 (2013.01); B41C 2210/08 (2013.01); B41C 2210/22 (2013.01); B41C 2210/24 (2013.01); G03F 7/004 (2013.01); G03F 7/0045 (2013.01)

(58) Field of Classification Search
CPC ....................................................... G03F 7/20
See application file for complete search history.

(56) References Cited

U.S. PATENT DOCUMENTS

| 3,969,119 A | 7/1976 | Muzyczko et al. |
| 4,077,806 A * | 3/1978 | Muzyczko .............. G03F 7/027 430/286.1 |
| 4,782,005 A | 11/1988 | Eklund et al. |
| 2007/0105041 A1* | 5/2007 | Loccufier .............. B41C 1/1041 430/270.1 |
| 2009/0142702 A1 | 6/2009 | Ray et al. |

FOREIGN PATENT DOCUMENTS

| EP | 0 243 208 A2 | 10/1987 |
| EP | 0 371 640 A1 | 6/1990 |
| EP | 0 378 429 A2 | 7/1990 |

OTHER PUBLICATIONS

Official Communication issued in International Patent Application No. PCT/EP2014/077175, dated Apr. 2, 2015.
Steenackers et al., "A Lithographic Printing Plate Precursor," U.S. Appl. No. 14/889,885, filed Nov. 9, 2015.
Loccufier et al., "A Lithographic Printing Plate Precursor," U.S. Appl. No. 14/889,884, filed Nov. 9, 2015.

* cited by examiner

*Primary Examiner* — Chanceity N Robinson
(74) *Attorney, Agent, or Firm* — Keating and Bennett, LLP

(57) ABSTRACT

A lithographic printing plate precursor includes (i) a support having a hydrophilic surface or which is provided with a hydrophilic layer, and (ii) a coating including a photopolymerisable layer, characterised in that the photopolymerisable layer includes a compound including at least one free radically polymerisable group and at least one moiety having a structure according to Formula (I):

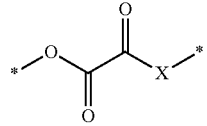

Formula (I)

wherein X represents O or NR* and R* represents hydrogen, an optionally substituted alkyl, aryl, aralkyl or heteroaryl group; and * denotes the linking positions to the rest of the compound.

12 Claims, 1 Drawing Sheet

Table 6: evaluation of a gum developer after processing.

| Evaluation | PP-B *comparative* | PP-A *inventive* |
|---|---|---|
| Average sludge (g/kg) | 14.54 | 3.36 |
| Microscope (100 x) | | |
| Cleanliness processor (1) | 3.0 | 1.5 |

(1) visual assessment whereby 0= clean processor, 5= contaminated processor; a value of 2 or below 2 is an acceptable value for cleanliness.

ns upon expo-
LITHOGRAPHIC PRINTING PLATE PRECURSOR

CROSS-REFERENCE TO RELATED APPLICATIONS

This application is a 371 National Stage Application of PCT/EP2014/077175, filed Dec. 10, 2014. This application claims the benefit of European Application No. 13196658.2, filed Dec. 11, 2013, which is incorporated by reference herein in its entirety.

BACKGROUND OF THE INVENTION

1. Field of the Invention

The present invention relates to a novel monomer and a negative-working lithographic printing plate precursor.

2. Description of the Related Art

Lithographic printing presses use a so-called printing master such as a printing plate which is mounted on a cylinder of the printing press. The master carries a lithographic image on its surface and a print is obtained by applying ink to said image and then transferring the ink from the master onto a receiver material, which is typically paper. In conventional, so-called "wet" lithographic printing, ink as well as an aqueous fountain solution (also called dampening liquid) are supplied to the lithographic image which consists of oleophilic (or hydrophobic, i.e. ink-accepting, water-repelling) areas as well as hydrophilic (or oleophobic, i.e. water-accepting, ink-repelling) areas. In so-called driographic printing, the lithographic image consists of ink-accepting and ink-abhesive (ink-repelling) areas and during driographic printing, only ink is supplied to the master.

The so-called "analogue" printing plates are generally obtained by first applying a so-called computer-to-film (CtF) method, wherein various pre-press steps such as typeface selection, scanning, color separation, screening, trapping, layout and imposition are accomplished digitally and each color selection is transferred to graphic arts film using an imagesetter. After processing, the film can be used as a mask for the exposure of an imaging material called plate precursor and after plate processing, a printing plate is obtained which can be used as a master. Since about 1995, the so-called "computer-to-plate" (CtP) method has gained a lot of interest. This method, also called "direct-to-plate", bypasses the creation of film because the digital document is transferred directly to a printing plate precursor by means of a platesetter. A printing plate precursor for CtP is often called a digital plate.

The support of the lithographic printing plates are typically aluminum supports which have a hydrophilic surface or on which a hydrophilic layer has been provided. This hydrophilic surface and/or layer should improve the water acceptance of the non-printing areas of a lithographic printing plate and the repulsion of the printing ink in these areas. During developing the soluble portions of the coating should be easily removed whereby the surface of the support remains residue-free so that clean background areas are obtained during printing.

Digital plates can roughly be divided in three categories:
  (i) silver plates, working according to the silver salt diffusion transfer mechanism;
  (ii) photopolymer plates containing a photopolymerisable composition that hardens upon exposure to light and
  (iii) thermal plates of which the imaging mechanism is triggered by heat or by light-to-heat conversion.

Photopolymer printing plates rely on a working-mechanism whereby the coating—which typically includes free radically polymerisable compounds—hardens upon exposure. "Hardens" means that the coating becomes insoluble or non-dispersible in the developing solution and may be achieved through polymerization and/or crosslinking of the photosensitive coating upon exposure to light. Photopolymer plate precursors can be sensitized to blue, green or red light i.e. wavelengths ranging between 450 and 750 nm, to violet light i.e. wavelengths ranging between 350 and 450 nm or to infrared light i.e. wavelengths ranging between 750 and 1500 nm. Optionally, the exposure step is followed by a heating step to enhance or to speed-up the polymerization and/or crosslinking reaction. The presslife of photopolymer plates is related to the cohesive strength within the polymerized photolayer. The higher the cohesive strength, the higher the presslife. The cohesive strength can preferably be improved by increasing the crosslinking degree and/or by supramolecular non-covalent interactions such as H-bonding, Van der Waals interaction and dipole-dipole interactions.

In general, a toplayer or protective overcoat layer over the imageable layer is required to act as an oxygen barrier to provide the desired sensitivity to the plate. A toplayer typically includes water-soluble or water-swellable polymers such as for example polyvinylalcohol. Besides acting as barrier for oxygen, the toplayer should best be easily removable during processing and be sufficiently transparent for actinic radiation, e.g. from 300 to 450 nm or from 450 to 750 nm or from 750 to 1500 nm.

The classical workflow of photopolymer plates involves first an exposure step of the photopolymer printing plate precursor in a violet or infrared platesetter, followed by an optional pre-heat step, a wash step of the protective overcoat layer, an alkaline developing step, and a rinse and gum step. Over the past years, there is a clear evolution in the direction of a simplified workflow where the pre-heat step and/or wash step are eliminated and where the processing and gumming step are carried out in one single step. However, development of photopolymer plates with a so-called development/gumming solution which typically has a lower pH than the conventional alkaline developer solution, becomes much more critical. Indeed, photopolymer plates generally include rather hydrophobic monomers and/or polymeric binders in order to obtain sufficient lithographic latitude on press. Sufficient lithographic latitude on press means that the plate maintains a clear differentiation in ink acceptance between image and non-image areas upon printing. However, due to the limited solubility of these hydrophobic components in a gum solution, considerable amounts of surfactant are needed to disperse these hydrophobic compounds in the gum solution. This often leads to an unacceptable increase in viscosity of the gum solution causing plate skewing and the formation of a thick gum layer on the plate. Decreasing the amount of surfactant results in an unacceptable formation of sludge in the batch processor, speckles on the plate and deposits in the clean-out unit, and this already at low exhaustion level. Although the use of more hydrophilic monomers or polymeric binders in the coating of the photopolymer plate improves the gum processability and exhaustion behaviour of the plate, it also results in an unacceptable blinding on press. Therefore, there is an urgent need for monomers and/or binders in negative-working photosensitive lithographic printing plates which provide both a good lithographic latitude on press and an enhanced gum processability and which minimise or even avoid the formation of sludge and precipitate and/or deposit materials in the developer solution during the processing.

U.S. Pat. No. 4,782,005 discloses a radiation sensitive composition comprising an acrylic or methacrylic acid ester, a photoinitiator, and a small amount of the additive N,N'-diorgano dicarboxamide. The radiation sensitive composition is sensitive to ultraviolet light and the N,N'-diorgano dicarboxamide is present in the composition in a minor amount ranging between 1 and 10% wt.

US 2009/0142702 discloses a method for making a light sensitive, negative-working photopolymer printing plate which is gum processable by including in the coating a specific compound including two hydroxyl groups.

SUMMARY OF THE INVENTION

It is an object of the present invention to provide a negative-working lithographic printing plate precursor including a photopolymerisable layer which provides a printing plate with an excellent lithographic latitude on press combined with an improved gum processability.

A negative-working lithographic printing plate precursor includes a support having a hydrophilic surface or which is provided with a hydrophilic layer, and a coating including a photopolymerisable layer comprising a compound comprising at least one free radically polymerisable group and at least one moiety having a structure according to Formula (I):

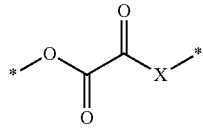

Formula (I)

wherein X represents O or NR* and wherein R* represents hydrogen, or an optionally substituted alkyl, aryl, aralkyl or heteroaryl group; and * denotes the linking positions to the rest of the compound.

It is a further object of the present invention to provide a method for making a heat-sensitive lithographic printing plate whereby excellent printing properties are obtained and whereby during the processing step the formation of organic sludge and precipitate and/or deposit materials in the developer solution is minimised or even avoided.

It was surprisingly found that the solubility of the components present in a developer solution including the non-image areas of the coating is significantly improved. With an improved solubility of the components present in a developer solution and/or stability of a developer solution is meant that the tendency of the developer to form precipitate (i.e. organic sludge) and/or deposit materials is reduced.

According to the present invention, there is also provided a new class of monomers represented by Formula (IX):

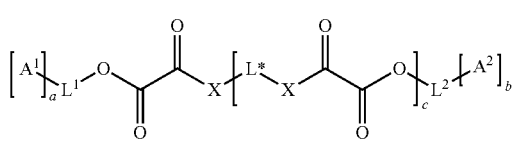

Formula (IX)

wherein
$L^1$, $L^2$, $L^*$, X, a, b, c, are as defined above; and
$A^1$ and $A^2$ independently represent acrylamide, methacrylamide or a terminal group;

with the proviso that at least one of $A^1$ or $A^2$ represents acrylamide or methacrylamide.

It was surprisingly found that the monomer according to Formula (IX) provides to the coating of a printing plate an excellent sensitivity—even without the presence of an overcoat—and highly improves the solubility of the components present in a developer solution including the non-image areas of a coating of a printing plate.

Other features, elements, steps, characteristics and advantages of the present invention will become more apparent from the following detailed description of preferred embodiments of the present invention. Specific preferred embodiments of the invention are also defined in the dependent claims.

BRIEF DESCRIPTION OF THE DRAWINGS

The FIGURE shows evaluation of a gum developer after processing.

DETAILED DESCRIPTION OF THE PREFERRED EMBODIMENTS

The lithographic printing plate precursor according to a preferred embodiment of the present invention is negative-working and includes a compound comprising at least one free radically polymerisable group and at least one moiety having a structure according to Formula (I):

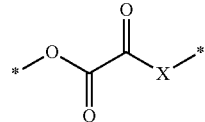

Formula (I)

wherein
X represents O or NR* and wherein R* represents hydrogen, an optionally substituted alkyl, aryl, aralkyl or heteroaryl group; and
* denotes the linking positions to the rest of the compound. Preferably, R* represents hydrogen or a $C_1$ to $C_{12}$-alkyl group.

The compound used in present invention may include one, two or more free radically polymerisable groups. Preferably the compound used in the present invention includes two free radically polymerisable groups. The free radically polymerisable groups present in the compound used in the present invention may be the same or different groups; preferably, they are the same groups. The free radical polymerisable group is preferably represented by an ethylenical unsaturated group. The ethylenical unsaturated group preferably represents an optionally substituted acrylate, methacrylate, acrylamide, methacrylamide, styrene, maleate, fumarate, itaconate, vinyl ether, vinyl ester, allyl ether and allyl ester group. More preferably, the free radically polymerisable group represents an optionally substituted acrylate, methacrylate, acrylamide, methacrylamide and/or a vinyl ether group. In a highly preferred embodiment, the free radically polymerisable group represents acrylamide or methacrylamide. The optional substituents may represent a halogen such as a fluoro, chloro, bromo or iodo atom or an alkyl group such as a methyl, ethyl, propyl or isopropyl group.

The compound used in the present invention can be a monomer, an oligomer (i.e. a structure including a limited amount of monomers such as two, three or four repeating units) or a polymer (i.e. a structure including more than four repeating units). The compound used in the present invention contains at least one moiety according to Formula (I), preferably 1 to 150 moieties according to Formula (I), more preferably 1 to 100 moieties according to Formula (I) and most preferably 1 to 10 moieties according to Formula (I). According to a preferred embodiment, the compound according to Formula (I) is part of the backbone of a polymer. Alternatively, the compound according to Formula (I) may be present in the side chain of a polymer. In a highly preferred embodiment, the compound used in the present invention comprises one, two, three or four moieties according to Formula (I).

The compound used in the present invention is preferably represented by the following Formula (II):

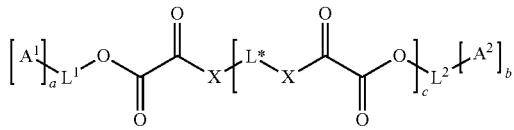

Formula (II)

wherein $L^1$ and $L^2$ are independently a divalent, trivalent, fourvalent, fivevalent or sixvalent linking group;

L* represents a divalent linking group;

X is as defined above for Formula (I);

$A^1$ and $A^2$ independently represent an ethylenical unsaturated group or a terminal group;

a represents 1, 2, 3, 4 or 5 respectively for a divalent, trivalent, fourvalent, fivevalent or sixvalent linking group $L^1$;

b represents 1, 2, 3, 4 or 5 respectively for a divalent, trivalent, fourvalent, fivevalent or sixvalent linking group $L^2$ c is an integer ranging from 0 to 150;

$A^1$ and $A^2$ may independently represent a group including a free radical polymerisable group as described above or a terminal group. The terminal group may be represented by hydrogen, an optionally substituted alkyl, aryl, aralkyl or heteroaryl group. Most preferably the terminal group represents a $C_1$ to $C_6$-alkyl group. The compound used in the present invention may include one, two, three, four or five $A^1$ groups repectively for a divalent, trivalent, fourvalent, fivevalent or sixvalent linking group $L^1$; and one, two, three, four or five $A^2$ groups repectively for a divalent, trivalent, fourvalent, fivevalent or sixvalent linking group $L^2$. In a preferred embodiment the linking groups $L^1$ and $L^2$ are divalent, trivalent or fourvalent and the compound used in the present invention includes one, two, three or four Al groups repectively for a divalent, trivalent or fourvalent linking group $L^1$; and one, two, three or four $A^2$ groups repectively for a divalent, trivalent or fourvalent linking group $L^2$.

c preferably represents an integer ranging between 0 and 100, more preferably an integer ranging between 0 and 10 and most preferably c represents 0, 1, 2, 3 or 4.

The linking groups $L^1$ and $L^2$ may be divalent, trivalent, fourvalent, fivevalent or sixvalent and are preferably independently selected from an optionally substituted alkylene or cycloalkylene group, an optionally substituted arylene or heteroarylene, —O—, —CO—, —CO—O—, —O—CO—, —CO—NH—, —NH—CO—, >N—CO—, —CO—N<, —NH—CO—O—, >N—CO—O—, —O—CO—NH—, —O—CO—N<, —NH—CO—NH—, >N—CO—NH—, —NH—CO—N<, >N—CO—N<, —NH—CS—NH—, >N—CS—NH—, —NH—CS—N<, >N—CS—N<, —CO—NR'—, —NR"—CO—, —(CH$_2$—CH$_2$—O)$_e$—, —SO—, —SO$_2$—, —SO$_2$—NH—, —SO$_2$—N<, —NH—SO$_2$—, >N—SO$_2$—, —CH═N—, >C═N—, —NH—NH—, >N—NH—, —NH—N<, >N—N<, —N$^+$(CH$_3$)$_2$—, —N$^+$(CH$_3$)<, >N$^+$(CH$_3$)—, >N$^+$<, —S—, —S—S—, —NH—CO—CO—NH—, —NH—CO—CO—N<, >H—CO—CO—NH—, >N—CO—CO—N<,

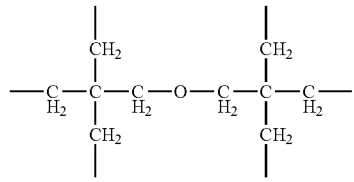

and/or combinations thereof, wherein e represents an integer greater than 1, preferably an integer ranging between 2 and 100, and wherein R' and R" each independently represent an optionally substituted alkyl, aryl, aralkyl or heteroaryl group. The substituents optionally present on the alkylene, arylene or heteroarylene group may be represented by an alkyl group such as a methyl, ethyl, propyl or isopropyl group, a halogen such as fluoro, chloro, bromo or iodo group, a hydroxyl group, an amino group, a (di)alkylamino group, or an alkoxy group such as a methoxy or ethoxy group.

The alkylene group as referred to in the above paragraph may be represented by the fourvalent Formula (III) or the trivalent Formula (IV):

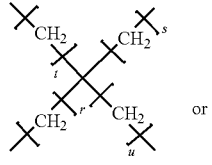

Formula (III)

or

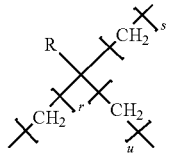

Formula (IV)

wherein r, s, t and u independently represent 0 or an integer greater than 0; preferably an integer ranging between 0 and 20, more preferably between 0 and 10, most preferably r, s, t and u independently represent an integer selected from 0 1, 2, 3, 4, 5 or 6; and R represents hydrogen, an alkyl, aralkyl, aryl or heteroaryl group.

More preferably, the alkylene group is divalent and represented by —(CH$_2$)$_p$— wherein p represents 1, or an integer greater than 1, preferably an integer ranging between 1 and 20, more preferably between 1 and 10, most preferably p represents an integer selected from 1, 2, 3, 4, 5 or 6.

In a preferred embodiment, the linking groups $L^1$ and $L^2$ are divalent and are preferably independently selected from an optionally substituted divalent alkylene group as described above, an optionally substituted arylene or heteroarylene, —O—, —CO—, —CO—O—, —O—CO—, —CO—NH—, —NH—CO—, —NH—CO—O—, —O—CO—NH—, —NH—CO—NH—, —NH—CS—NH—, —CO—NR'—, —NR"—CO—, —(CH$_2$—CH$_2$—O)$_e$—, —SO—, —SO$_2$—, —SO$_2$—NH—, —NH—SO$_2$—, —CH=N—, —NH—NH—, —N$^+$(CH$_3$)$_2$—, —S—, —S—S—, —NH—CO—CO—NH— and/or combinations thereof, wherein e represents an integer greater than 1, preferably an integer ranging between 2 and 100, and wherein R' and R" each independently represent an optionally substituted alkyl, aryl, aralkyl or heteroaryl group. The substituents optionally present on the alkylene, arylene or heteroarylene group may be represented by an alkyl group such as a methyl, ethyl, propyl or isopropyl group, a halogen such as fluoro, chloro, bromo or iodo group, a hydroxyl group, an amino group, a (di)alkylamino group, or an alkoxy group such as a methoxy or ethoxy group.

More preferably, the linking groups $L^1$ and $L^2$ independently represent a divalent aliphatic group including straight or branched carbon chain(s) or alicyclic, non-aromatic ring(s). Optionally the aliphatic linking group may contain substituents including for example oxygen or sulfur; alkyl groups such as a methyl, ethyl, propyl or isopropyl group and halogens such as a fluoro, chloro, bromo or iodo atom.

Most preferably, the linking groups $L^1$ and $L^2$ independently represent an optionally substituted divalent alkylene group. The substituents optionally present on the divalent alkylene group may be represented by an alkyl group such as a methyl, ethyl, propyl or isopropyl group or a halogen such as a fluoro, chloro, bromo or iodo atom.

The compound used in the present invention is more preferably represented by the following Formula (V):

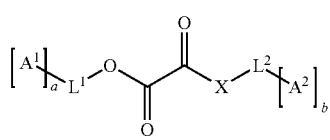

Formula (V)

wherein $L^1$ and $L^2$, a and b, $A^1$ and $A^2$ and X are as defined for Formulae (I) and (II) above.

The compound used in the present invention is most preferably represented by the following Formula (VI):

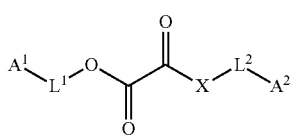

Formula (VI)

wherein $L^1$ and $L^2$ independently represent a divalent linking group as defined above, and $A^1$, $A^2$ and X are as defined for Formulae (I) and (II) above.

In a most preferred embodiment, $A^1$ and $A^2$ in the Formulae (II), (V) and (VI) independently represent acrylamide or methacrylamide.

In a preferred embodiment wherein the compound according to Formula (I) is present in the side chain of a polymer, the following moiety (Formula VII) is preferably attached to the polymer:

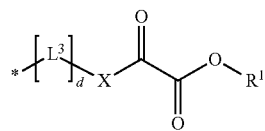

Formula (VII)

wherein

* denotes the linking to the polymer,

X is the same as defined above;

$L^3$ represents a divalent linking group, d represents 0 or 1, and $R^1$ represents a terminal group.

The terminal group $R^1$ preferably represents an optionally substituted alkyl, aryl, aralkyl or heteroaryl group or a free radical polymerisable group as described above. More preferably $R^1$ represents a $C_1$ to $C_{12}$-alkyl group or an aryl group. More preferably $R^1$ represents methyl, ethyl, t-butyl, isopropyl, or phenyl.

The linking group $L^3$ has the same meaning as described above for the linking groups $L^1$ and $L^2$. Most preferably the linking group $L^3$ represents an optionally substituted divalent alkylene group.

Polymers including the moiety according to Formula (VII) in the side chain may be obtained by the coupling reaction between a polymer bearing an alcohol group, a primary or secundary amino group and/or a combination thereof, and one or a combination of the following compounds:

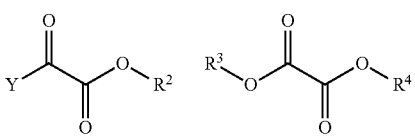

wherein

Y represents a halogen such as a fluoro, chloro, bromo or iodo atom, and $R^2$, $R^3$ and $R^4$ independently represent a terminal group.

The terminal group preferably represents an optionally substituted alkyl, aryl, aralkyl or heteroaryl group.

Polymers bearing an alcohol group, a primary or secundairy amino group can be selected from a wide series of organic polymers. Useful polymers and copolymers include for example polyvinyl alcohols, polyacetales, polyvinylacetates, cellulose derivatives, poly(2-hydroxyethyl methacrylate), poly(2-hydroxyethyl acrylate), polysiloxane derivatives such as copolymers of aminoalkylmethylsiloxane or hydroxyalkylmethylsiloxane, polyethyleneimine and polypropyleneimine.

Preferably, polymers including the moiety according to Formula (VII) in the side chain are obtained by the coupling reaction between oxalyl chloride, ethyl oxalyl chloride or diethyl oxalate with polymers or copolymers of polyvinyl alcohols, poly(2-hydroxyethyl methacrylate), poly(2-hydroxyethyl acrylate), polyethyleneimine or polypropyleneimine.

In the present invention, suitable alkyl groups include 1 or more carbon atoms such as for example $C_1$ to $C_{22}$-alkyl groups, more preferably $C_1$ to $C_{12}$-alkyl groups and most preferably $C_1$ to $C_6$-alkyl groups. The alkyl group may be lineair or branched such as for example methyl, ethyl, propyl (n-propyl, isopropyl), butyl (n-butyl, isobutyl, t-butyl), pentyl, 1,1-dimethyl-propyl, 2,2-dimethylpropyl and 2-methylbutyl, or hexyl. The alkyl group may be cyclic; suitable cycloalkyl groups are non-aromatic, homocyclic groups containing carbon atoms and may be monocyclic-or polycyclic. Examples include cyclopentyl, cyclohexyl or adamantyl.

In the present invention, suitable aryl groups include for example phenyl, naphthyl, benzyl, tolyl, ortho- meta- or para-xylyl, anthracenyl or phenanthrenyl.

In the present invention, suitable aralkyl groups include for example phenyl groups or naphthyl groups including one, two, three or more $C_1$ to $C_6$-alkyl groups.

In the present invention, suitable heteroaryl groups are preferably monocyclic- or polycyclic aromatic rings comprising carbon atoms and one or more heteroatoms in the ring structure. Preferably 1 to 4 heteroatoms are independently selected from nitrogen, oxygen, selenium and sulphur and/or combinations thereof. Examples include pyridyl, pyrimidyl, pyrazoyl, triazinyl, imidazolyl, (1,2,3,)- and (1,2,4)-triazolyl, tetrazolyl, furyl, thienyl, isoxazolyl, thiazolyl and carbazoyl.

The substituents optionally present on the alkyl, aralkyl, aryl or heteroaryl groups as described above are preferably selected from an alkyl, ester, amide, ether, thioether, ketone, aldehyde, hydroxyl, thiol, cyanide, nitro, amino, (di)alkylamino, alkoxy, sulfoxide, sulfone, sulfonate ester or sulphonamide group, a halogen such as fluoro, chloro, bromo or iodo atom, and/or combinations thereof. More preferably, the optional substituents are represented by a halogen such as a fluoro, chloro, bromo or iodo atom, a hydroxyl group, an amino group, a (di)alkylamino group or an alkoxy group.

Without being limited thereto, typical examples of the compounds used in the present invention are given below.

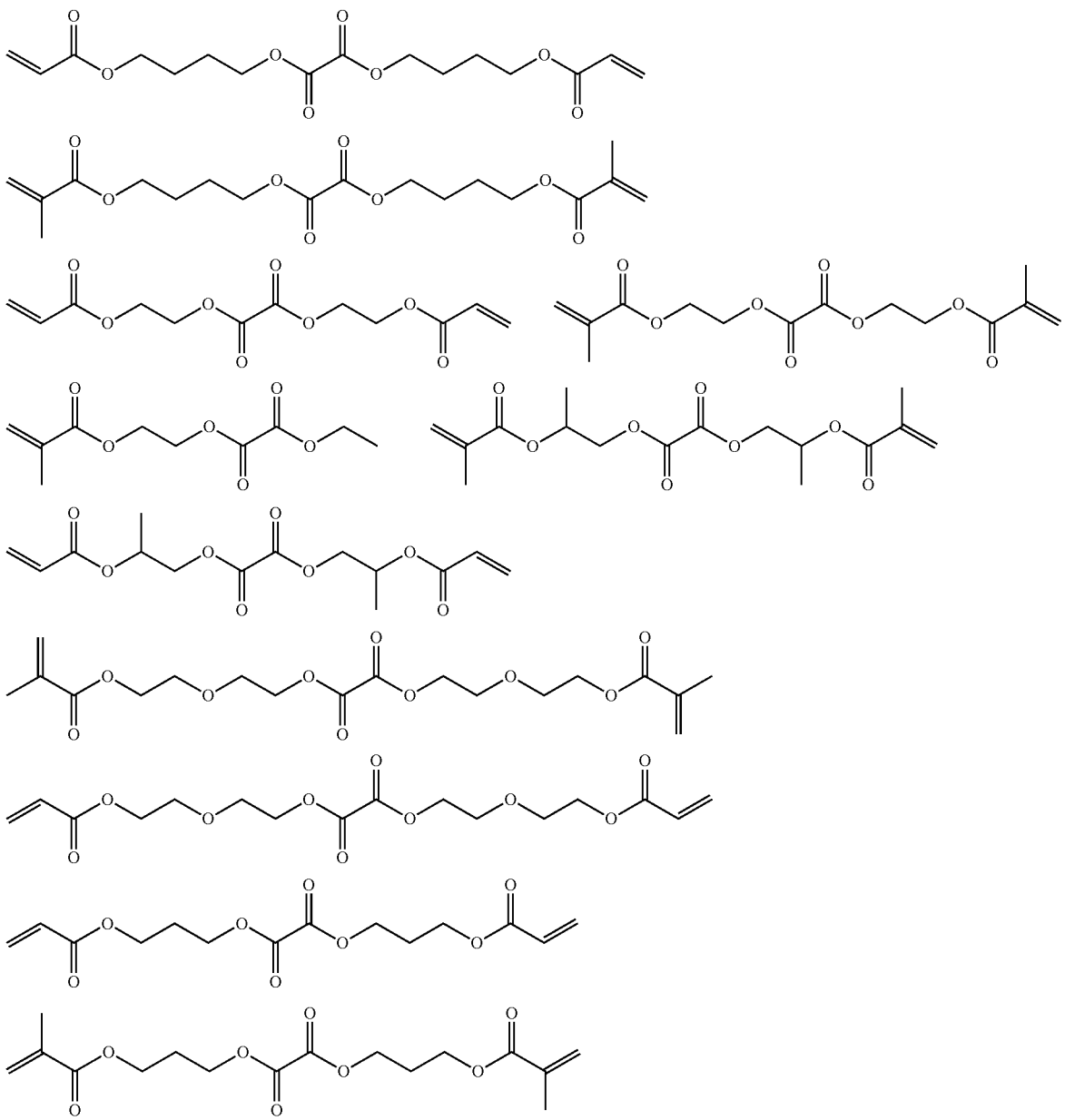

-continued
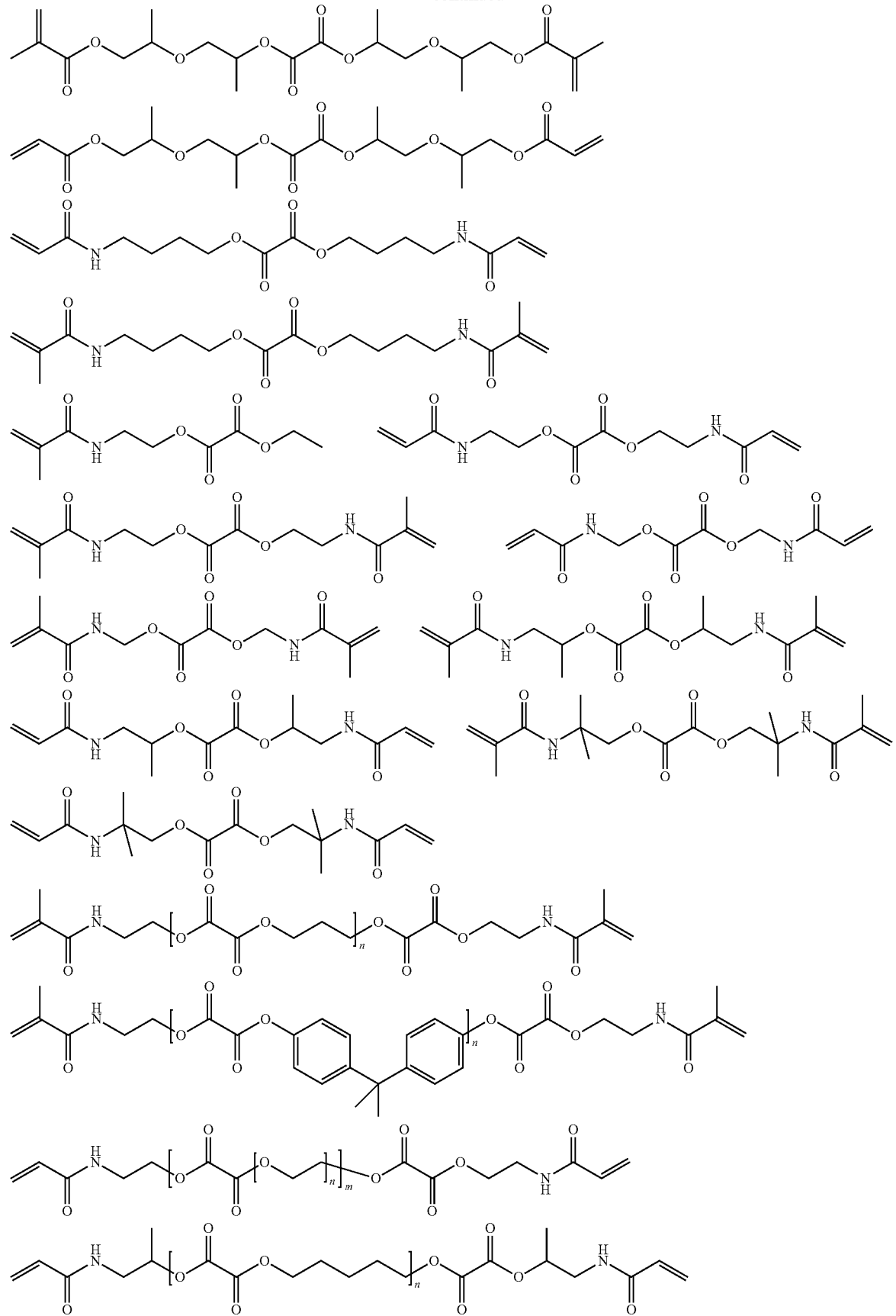

-continued
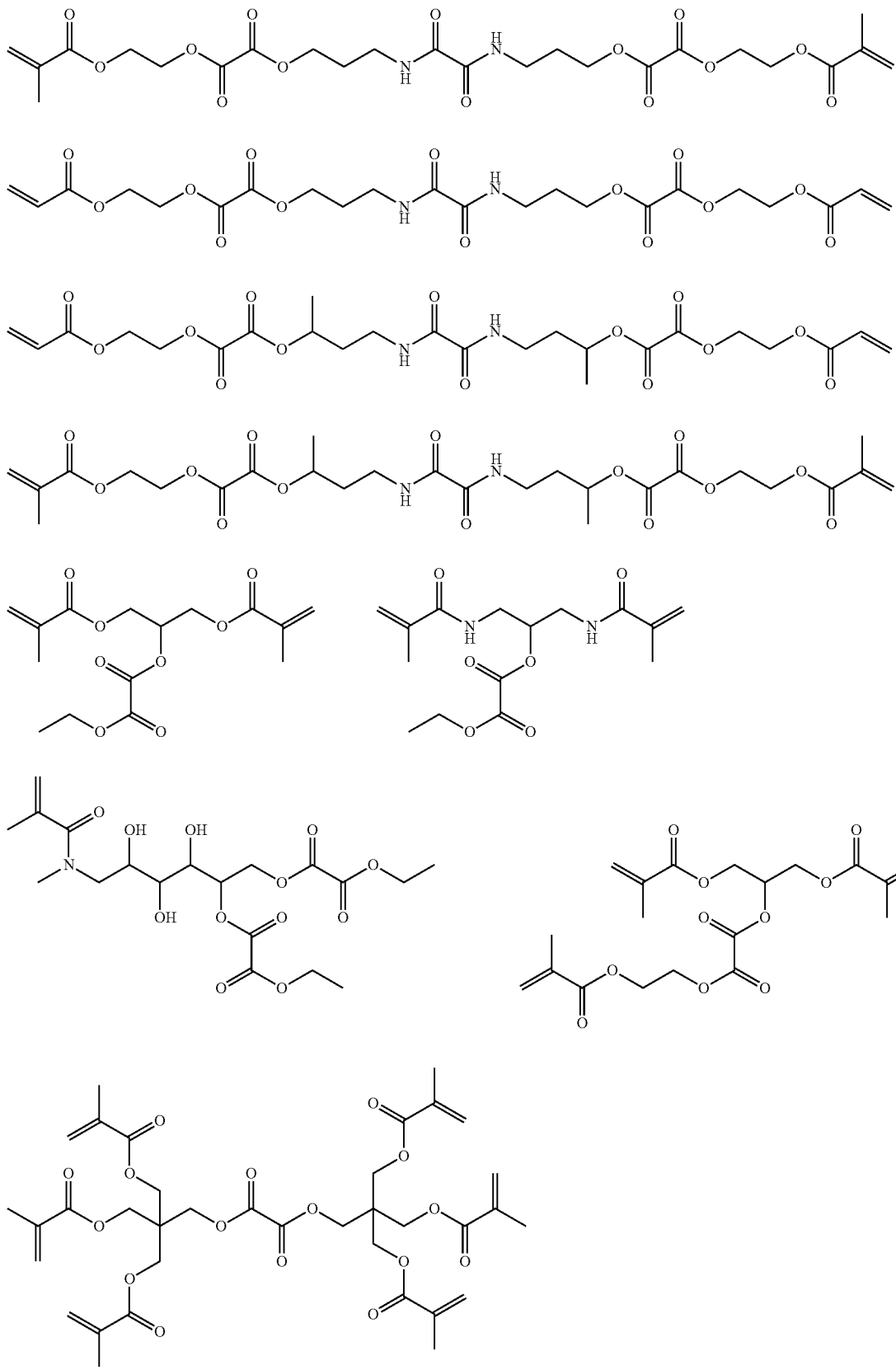

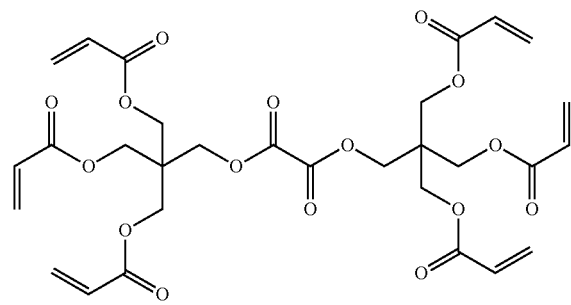
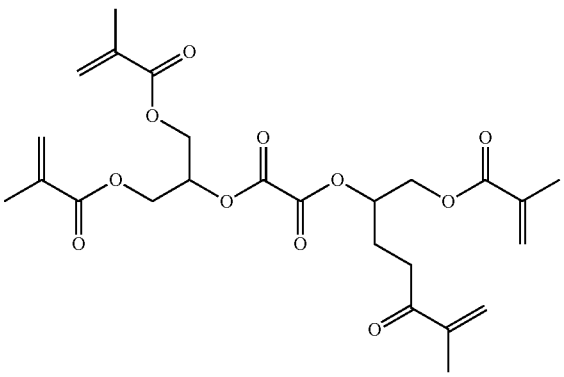
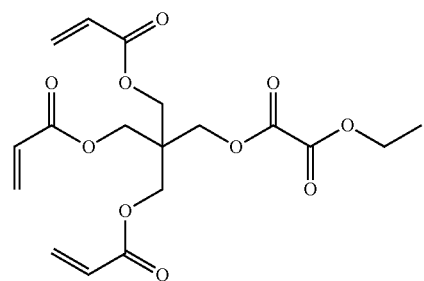
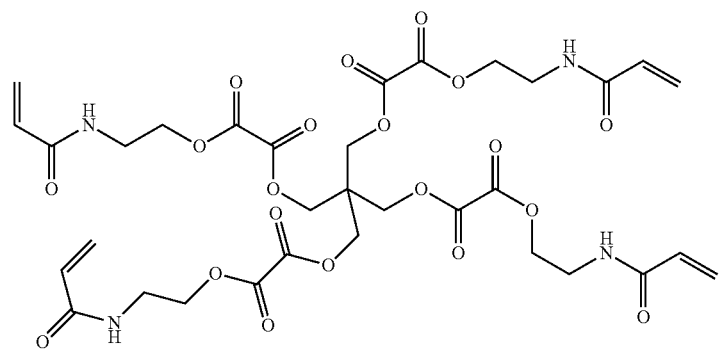
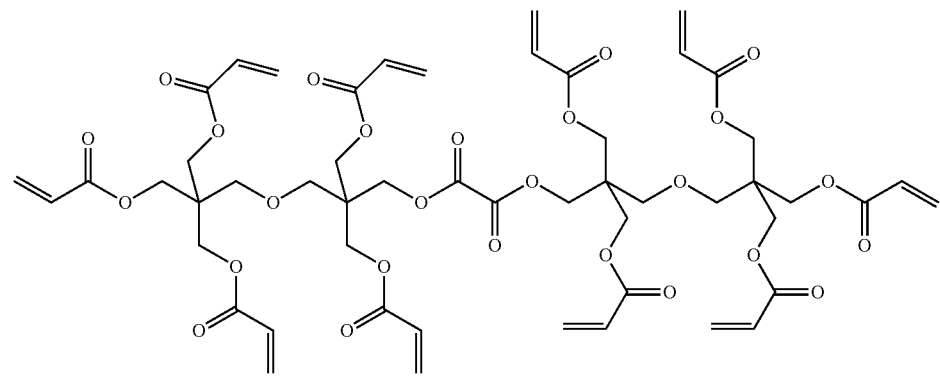
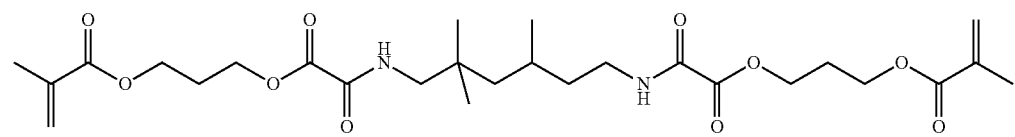
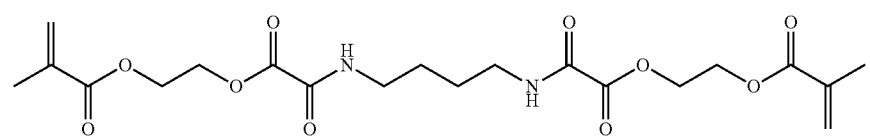

-continued
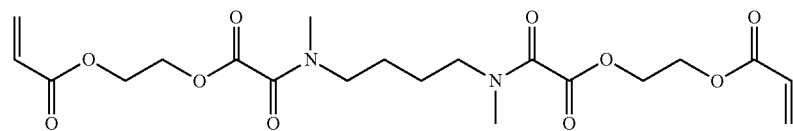
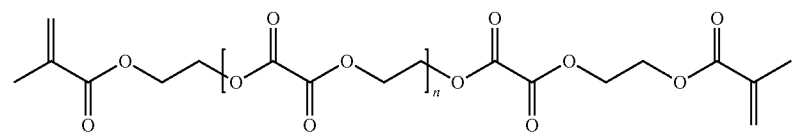
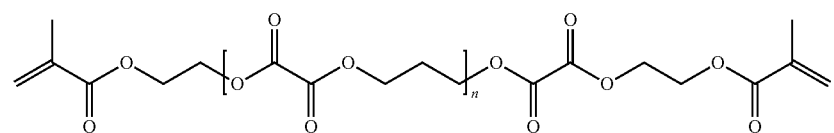
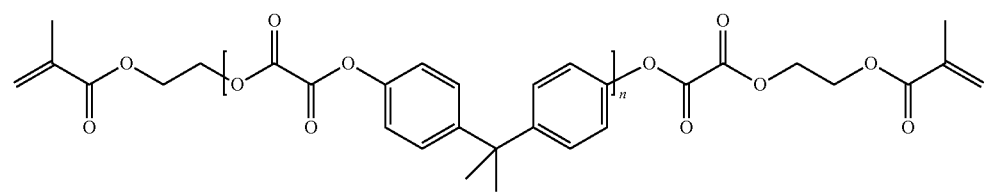
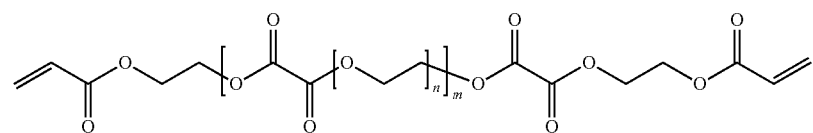
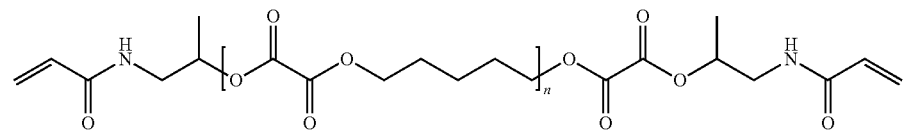
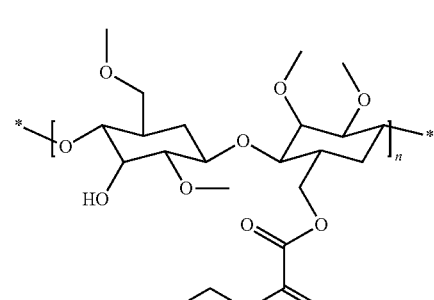
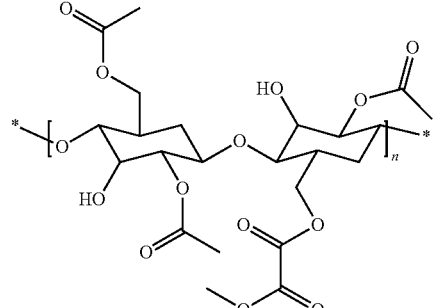
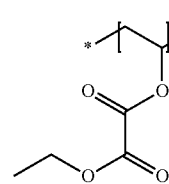
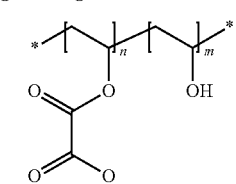
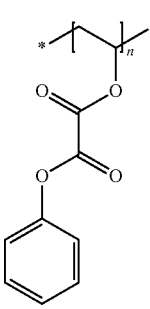
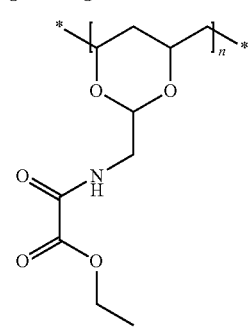

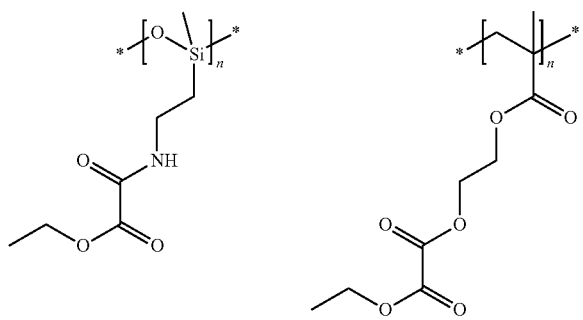
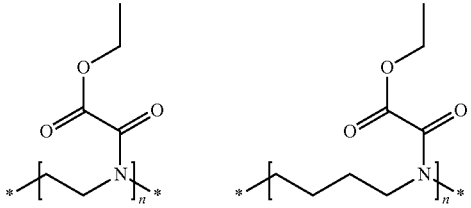

Wherein n=1 to 100 and m=1 to 100

According to the present invention, there is also provided a new class of monomers represented by Formula (IX):

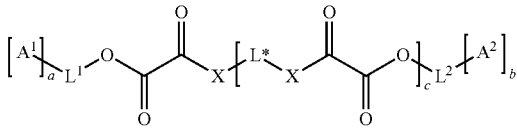

Formula (IX)

wherein

L$^1$, L$^2$, L*, X, a, b, c, are as defined above; and

A$^1$ and A$^2$ independently represent acrylamide, methacrylamide or a terminal group;

with the proviso that at least one of A$^1$ or A$^2$ represents acrylamide or methacrylamide.

The terminal group may be represented by hydrogen, an optionally substituted alkyl, aryl, aralkyl or heteroaryl group. Most preferably the terminal group represents a C$_1$ to C$_6$-alkyl group. The compound used in the present invention may include one, two or three A$^1$ groups repectively for a divalent, trivalent and fourvalent linking group L$^1$; and one, two or three A$^2$ groups repectively for a divalent, trivalent and fourvalent linking group L$^2$.

The monomer according to the present invention is more preferably represented by the following Formula (X):

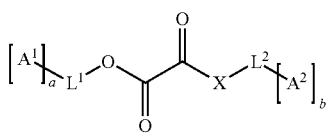

Formula (X)

wherein

L$^1$ and L$^2$, a and b and A$^1$ and A$^2$ and X are as defined above for Formula (VIII).

The monomer according to the present invention is most preferably represented by the following Formula (XI):

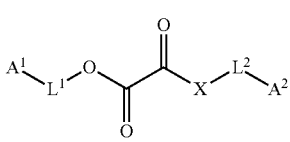

Formula (XI)

wherein L$^1$ and L$^2$ independently represent a divalent linking group as defined and A$^1$, A$^2$ and X are as defined above for Formulae (IX) and (X).

The lithographic printing plate precursor according to the present invention is negative-working, i.e. after exposure and development the non-exposed areas of the coating are removed from the support and define hydrophilic (non-printing) areas, whereas the exposed coating is not removed from the support and defines oleophilic (printing) areas. The hydrophilic areas are defined by the support which has a hydrophilic surface or is provided with a hydrophilic layer. The hydrophobic areas are defined by the coating, hardened upon exposing, optionally followed by a heating step. Areas having hydrophilic properties means areas having a higher affinity for an aqueous solution than for an oleophilic ink; areas having hydrophobic properties means areas having a higher affinity for an oleophilic ink than for an aqueous solution.

"Hardened" means that the coating becomes insoluble or non-dispersible for the developing solution and may be achieved through polymerization and/or crosslinking of the photosensitive coating, optionally followed by a heating step to enhance or to speed-up the polymerization and/or cross-linking reaction. In this optional heating step, hereinafter also referred to as "pre-heat", the plate precursor is heated, preferably at a temperature of about 80° C. to 150° C. and preferably during a dwell time of about 5 seconds to 1 minute.

The coating has at least one layer including a photopolymerisable composition, said layer is also referred to as the "photopolymerisable layer". The coating may include an intermediate layer, located between the support and the photopolymerisable layer.

The amount of the compound used in the present invention or of the compound according to the present invention in the photopolymerisable layer is preferably above 1% wt, more preferably above 2% wt and most preferably above 5% wt relative to the total weight of all ingredients in the photopolymerisable layer. Alternatively, the compound used in the present invention in the photopolymerisable layer is preferably between 1 and 90% wt, more preferably between 5% wt and 80% wt, even more preferably between 10 and 70% wt, and most preferably between 40 and 60% wt, relative to the total weight of all ingredients in the photopolymerisable layer.

The photopolymerisable layer includes, besides the compound used in the present invention and/or the compound according to the present invention, optionally a polymerisable compound, optionally a binder, a polymerization initiator capable of hardening said further polymerisable compound in the exposed areas, and optionally a sensitizer capable of absorbing light used in the image-wise exposing step. The photopolymerisable layer has a coating thickness preferably ranging between 0.2 and 5.0 g/m$^2$, more preferably between 0.4 and 3.0 g/m$^2$, most preferably between 0.6 and 2.2 g/m$^2$.

According to a preferred embodiment, the polymerisable compound is a monomer or oligomer including at least one epoxy or vinyl ether functional group and the polymerisation initiator is a Brönsted acid generator capable of generating free acid, optionally in the presence of a sensitizer, upon exposure, hereinafter the Brönsted acid generator is also referred to as "cationic photoinitiator" or "cationic initiator".

Suitable polyfunctional epoxy monomers include, for example, 3,4-epoxycyclohexylmethyl-3,4-epoxycyclohexane carboxylate, bis-(3,4-epoxycyclohexymethyl)adipate, difunctional bisphenol A-epichlorohydrin epoxy resin and multifunctional epichlorohydrintetraphenylol ethane epoxy resin.

Suitable cationic photoinitiators include, for example, triarylsulfonium hexafluoroantimonate, triarylsulfonium hexafluorophosphate, diaryliodonium hexafluoroantimonate, and haloalkyl substituted s-triazine. It is noted that most cationic initiators are also free radical initiators because, in addition to generating Brönsted acid, they also generate free radicals during photo or thermal decomposition.

According to a more preferred embodiment of the present invention, the polymerisable compound is a polymerisable monomer or oligomer including at least one terminal ethylenic group, hereinafter also referred to as "free-radical polymerisable monomer", and the polymerisation initiator is a compound capable of generating free radicals upon exposure, optionally in the presence of a sensitizer, hereinafter said initiator is referred to as "free radical initiator". The polymerisation involves the linking together of the free-radical polymerisable monomers.

Suitable free-radical polymerisable monomers include, for example, multifunctional (meth)acrylate monomers (such as (meth)acrylate esters of ethylene glycol, trimethylolpropane, pentaerythritol, ethoxylated ethylene glycol and ethoxylated trimethylolpropane, multifunctional urethanated (meth)acrylate, and epoxylated (meth)acrylate), and oligomeric amine diacrylates. The (meth)acrylic monomers may also have other double bond or epoxide group, in addition to (meth)acrylate group. The (meth)acrylate monomers may also contain an acidic (such as carboxylic acid) or basic (such as amine) functionality.

Any free radical initiator capable of generating free radicals upon exposure directly or in the presence of a sensitizer, is according to this invention a suitable initiator. Suitable free-radical initiators are described in WO 2005/111727 from page 15 line 17 to page 16 line 11.

In a preferred embodiment of the present invention the photopolymerisable composition comprises a hexaaryl-bisimidazole compound (HABI; dimer of triaryl-imidazole) as polymerisation initiator, optionally in combination with further polymerisation initiators.

A procedure for the preparation of hexaarylbisimidazoles is described in DE 1470 154 and their use in photopolymerisable compositions is documented in EP 24 629, EP 107 792, U.S. Pat. No. 4,410,621; EP 215 453 and DE 3 211 312. Preferred derivatives are e.g. 2,4,5,2',4',5'-hexaphenylbisimidazole, 2,2'-bis(2-chlorophenyl)-4,5,4',5'-tetraphenylbisimidazole, 2,2'-bis(2-chlorophenyl)-4,5,4',5'-tetrakis(3-methoxyphenyl)bisimidazole and 2,2'-bis(2-nitrophenyl)-4,5,4',5'-tetraphenylbisimidazole. The amount of the HABI polymerization initiator typically ranges from 0.01 to 30% by weight, preferably from 0.5 to 20% by weight, relative to the total weight of the non volatile components of the photopolymerisable composition.

A very high sensitivity can be obtained in the context of the present invention by the combination of an optical brightener as sensitizer and a hexaarylbisimidazole compound as polymerisation initiator.

Suitable classes of polymerisation initiators other than hexaarylbisimidazole compounds include aromatic ketones, aromatic onium salts, organic peroxides, thio compounds, ketooxime ester compounds, borate compounds, azinium compounds, metallocene compounds, active ester compounds and compounds having a carbon-halogen bond, but preferably the composition comprises a non-boron comprising polymerisation initiator and particularly preferred the polymerisation initiator comprises no boron compound. Many specific examples of initiators suitable for the present invention can be found in EP-A 1 091 247. Other preferred polymerization initiators are trihalo methyl sulphones.

Preferably hexaarylbisimidazole compounds and/or metallocene compounds are used alone or in combination with other suitable photoinitiators, in particular with aromatic ketones, aromatic onium salts, organic peroxides, thio compounds, ketooxime ester compounds, azinium compounds, active ester compounds or compounds having a carbon halogen bond.

In a preferred embodiment of the present invention the hexaarylbisimidazole compounds make more than 50 mol %, preferably at least 80 mol % and particularly preferred at least 90 mol % of all the photoinitiators used in the photopolymerisable composition of the present invention.

According to another preferred embodiment of the present invention, the polymerisable monomer or oligomer may be a combination of a monomer or oligomer comprising at least one epoxy or vinyl ether functional group and a polymerisable ethylenically unsaturated compound having at least one terminal ethylenic group, and the polymerisation initiator may be a combination of a cationic initiator and a free-radical initiator. A monomer or oligomer comprising at least one epoxy or vinyl ether functional group and a polymerisable ethylenically unsaturated compound having at least one terminal ethylenic group, can be the same compound wherein the compound contains both the ethylenic group and the epoxy or vinyl ether group. Examples of such compounds include epoxy functional acrylic monomers, such as glycidyl acrylate. The free radical initiator and the cationic initiator can be the same compound if the compound is capable of generating both free radical and free acid. Examples of such compounds include various onium salts such as diaryliodonium hexafluoroantimonate, triarylsuffonium hexafluoroantimonate, and s-triazines such as 2,4-bis(trichloromethyl)-6-[(4-ethoxyethylenoxy)-phen-1-yl]-s-triazine which are capable of generating both free radical and free acid, preferably in the presence of a sensitizer.

The photopolymerisable layer may also comprise a multifunctional monomer. This monomer contains at least two functional groups selected from an ethylenically unsaturated group and/or an epoxy or vinyl ether group. Particular multifunctional monomers for use in the photopolymer coating are disclosed in U.S. Pat. Nos. 6,410,205, 5,049,479, EP 1 079 276 , EP 1 369 232, EP 1 369 231, EP 1 341 040 , US 2003/0124460 , EP 1 241 002, EP 1 288 720 and in the reference book including the cited references: Chemistry & Technology UV & EB formulation for coatings, inks & paints—Volume 2—Prepolymers and Reactive Diluents for UV and EB Curable Formulations by N. S. Allen, M. A.

Johnson, P. K. T. Oldring, M. S. Salim—Edited by P. K. T. Oldring—1991—ISBN 0 947798102. Particularly preferred are urethane (meth)acrylate multifunctional monomers, which can be used alone or in combination with other (meth)acrylate multifunctional monomers.

The photopolymerisable layer may also comprise a co-initiator. Typically, a co-initiator is used in combination with a free radical initiator and/or a cationic initiator. Suitable co-initiators for use in the photopolymer coating are disclosed in U.S. Pat. Nos. 6,410,205; 5,049,479; EP 1 079 276, EP 1 369 232, EP 1 369 231, EP 1 341 040, US 2003/0124460, EP 1 241 002, EP 1 288 720 and in the reference book including the cited refences: Chemistry & Technology UV & EB formulation for coatings, inks & paints—Volume 3—Photoinitiators for Free Radical and Cationic Polymerisation by K. K. Dietliker—Edited by P. K. T. Oldring—1991—ISBN 0 947798161. Specific co-initiators, as described in EP 107 792, may be present in the photopolymerizable layer to further increase the sensitivity. Preferred co-initiators are sulfur-compounds, especially thiols like e.g. 2-mercaptobenzothiazole, 2-mercaptobenzoxazole, 2-mercapto-benzimidazole, 4-methyl-3-propyl-1,2,4-triazoline-5-thione, 4-methyl-3-n-heptyl-1,2,4-triazoline-5-thione, 4-phenyl-3-n-heptyl-1,2,4-triazoline-5-thione, 4-phenyl-3,5-dimercapto-1,2,4-triazole, 4-n-decyl-3,5-dimercapto-1,2,4-triazole,5-phenyl-2-mercapto-1,3,4-oxadiazole, 5-methylthio-1,3,4-thiadiazoline-2-thione, 5-hexylthio-1,3,4-thiadiazoline-2-thione, mercaptophenyltetrazole, pentaerythritol mercaptopropionate, butyric acid-3-mercapto-neopentanetetrayl ester, pentaerythritol tetra(thioglycolate).

Other preferred co-initiators are polythioles as disclosed in WO 2006/048443 and WO 2006/048445. These polythiols may be used in combination with the above described thiols, e.g. 2-mercaptobenzthiazole.

The photopolymerisable layer may also comprise particles which increase the resistance of the coating against manual or mechanical damage. The particles may be inorganic particles, such as for example silica, alumina, iron oxides, magnesium carbonate, titanium oxide and calcium carbonate. The particles may be organic particles or fillers, such as for example polymer particles, waxes, carbon black and silicone resins. The particles preferably have a particle size of about 0.01 to 2 µm. More information on suitable particles is described in for example U.S. Pat. No. 7,108,956.

The photopolymerisable layer may also comprise organic or inorganic spacer particles which increase the resistance of the coating against manual or mechanical damage. The spacer particles have preferably a particle size larger than 0.5 µm, more preferably a particle size larger than 0.8 µm, most preferably equal to or larger than 1.0 µm. The particle size is preferably comprised between 0.5 µm and 15 µm, more preferably between 0.5 µm and 7 µm, most preferably between 1 µm and 5 µm. The particle size refers to the average particle size and may be measured by a laser diffraction particle analyzer such as the Coulter LS Particle Size Analyzer, e.g. the Coulter LS-230, commercially available by Beckman Coulter Inc. The average particle size is defined as the mean or median of the volume distribution of particle size.

For obtaining a significant effect of improving the resistance of the coating against manual or mechanical damage, the spacer particles should extend the surface of the coating. The coating has preferably a layer thickness greater than 0.5 g/m$^2$, more preferably the layer thickness is comprised between 0.6 g/m$^2$ and 2.8 g/m$^2$. The particle size of the spacer particles is preferably comprised between one to two times the thickness of the coating.

Examples of inorganic spacer particles include silicium, titanium, aluminium, zinc, iron, chromium or zirconium containing particles, metal oxides or hydroxides thereof, aluminiumsilicates, and metal salts such as calcium carbonate, barium sulfate, barium titanate and strontium titanate.

Examples of organic spacer particles include optionally cross-linked polyalkyl(meth)acrylate such as polymethylmethacrylate, polystyrene, melamine, polyolefins such as polyethylene or polypropylene, halogenated polyolefins such as fluorinated polyolefins for example polytetrafluoroethylene, silicones such as cross-linked polysiloxane particles, or copolymers thereof. Examples of polysiloxane particles include cross-linked polyalkylsiloxanes such as polymethylsiloxane. Commercially available cross-linked polysiloxane particles are for example Tospearl from TOSHIBA SILICONE Co.,Ltd.

The photopolymerizable layer may also comprise an inhibitor. Particular inhibitors for use in the photopolymer coating are disclosed in U.S. Pat. No. 6,410,205, EP 1 288 720 and EP 1 749 240. The photopolymerizable layer may further comprise an adhesion promoting compound. More information on suitable adhesion promoting compounds are described in EP 1 788 434 in
and in the non-published patent application PCT/EP2013/055773.

Besides the compound used in the invention and/or the compound according to the present invention, the photopolymerizable layer may include a binder. The binder can be selected from a wide series of organic polymers. Compositions of different binders can also be used. Useful binders are described in WO2005/052298 page 17 line 21 to page 19 line 30, in EP 152 819 on page 2 line 50 to page 4 line 20, and in EP 1 043 627 in paragraph [0013].

The organic polymers used as binders have a typical average molecular weight $M_w$ between 1000 and 700 000, preferably between 1500 and 350 000. Preferably, the binders have a hydroxyl number between 0 and 750, more preferably between 10 and 500. Even more preferably the hydroxyl number is below 10, most preferably the hydroxyl number is 0. The amount of binder(s) generally ranges from 1 to 60% by weight, preferably 5 to 50% by weight, more preferably 10 to 35% by weight and most preferably 15 to 25% by weight relative to the total weight of the non-volatile components of the composition.

In another preferred embodiment the polymeric binder comprises a backbone including pendant groups such as for example a hydrophilic poly(alkylene oxide) segment. The polymeric binder may also include pendant cyano groups attached to the backbone. A combination of such binders may also be employed. Generally the polymeric binder is solid at room temperature, and is typically a non-elastomeric thermoplastic. Generally the polymeric binder is characterized by a number average molecular weight (Mn) in the range from about 500 to 250000, more commonly in the range from about 1000 to 240000 or 1500 to 200000. The polymerisable composition may comprise discrete particles of the polymeric binder. Preferably the discrete particles are particles of the polymeric binder which are suspended in the polymerisable composition. The presence of discrete particles tends to promote developability of the unexposed areas. Specific examples of the polymeric binders according to this preferred embodiment are described in U.S. Pat. No. 6,899,994; US 2004/0260050, US 2005/0003285, US 2005/0170286 and US 2005/0123853. In addition to the polymeric binder of this preferred embodiment the imageable layer may optionally comprise one or more co-binders. Typical co-binders are water-soluble or water-dispersible polymers, such as, cellulose derivatives, polyvinylalcohol, polyacrylic acid, poly(meth)acrylic acid, polyvinylpyrrolidone, polylactide, polyvinylphosphonic acid, synthetic co-polymers, such as co-polymers of an alkoxy polyethylene glycol (meth)acrylate. Specific examples of co-binders are described in US 2004/0260050, US 2005/0003285 and US 2005/0123853. Printing plate precursors, the imageable layer of which includes a binder and optionally a co-binder according to this preferred embodiment and described in more detail in US 2004/0260050, US 2005/0003285 and US 2005/0123853, optionally comprise a topcoat and an interlayer.

Various surfactants may be added into the photopolymerisable layer to allow or enhance the developability of the precursor; especially developing with a gum solution. Both polymeric and small molecule surfactants can be used. Nonionic surfactants are preferred. Preferred nonionic surfactants are polymers and oligomers containing one or more polyether (such as polyethylene glycol, polypropylene glycol, and copolymer of ethylene glycol and propylene glycol) segments. Examples of preferred nonionic surfactants are block copolymers of propylene glycol and ethylene glycol (also called block copolymer of propylene oxide and ethylene oxide); ethoxylated or propoxylated acrylate oligomers; and polyethoxylated alkylphenols and polyethoxylated fatty alcohols. The nonionic surfactant is preferably added in an amount ranging between 0.01 and 20% by weight of the coating, more preferably between 0.1 and 10% by weight of the coating, and most preferably between 0.5 and 5% by weight of the coating.

Suitable examples of optical brighteners as sensitizers are described in WO 2005/109103 page 24, line 20 to page 39. The photocurable composition may also comprise other sensitizers. Highly preferred sensitizers are violet light absorbing sensitizers, having an absorption spectrum between 350 nm and 450 nm, preferably between 370 nm and 420 nm, more preferably between 390 nm and 415 nm. Particular preferred sensitizers are disclosed in EP 1 349 006 paragraph [0007] to [0009], EP 1 668 417 and WO 2004/047930, including the cited references in these patent applications. Other highly preferred sensitizers are infrared light absorbing dyes, having an absorption spectrum between 750 nm and 1300 nm, preferably between 780 nm and 1200 nm, more preferably between 800 nm and 1100 nm. Particular preferred sensitizers are heptamethinecyane dyes, especially the dyes disclosed in EP 1 359 008 paragraph [0030] to [0032]. Other preferred sensitizers are blue, green or red light absorbing sensitizers, having an absorption spectrum between 450 nm and 750 nm. Useful sensitizers can be selected from the sensitizing dyes disclosed in U.S. Pat. Nos. 6,410,205; 5,049,479; EP 1 079 276, EP 1 369 232, EP 1 369 231, EP 1 341 040, US 2003/0124460, EP 1 241 002 and EP 1 288 720.

The photopolymerisable layer or an optional other layer of the coating may also comprise a colorant. After processing, at least part of the colorant remains on the hardened coating areas, and a visible image can be produced on the support by removing the coating, including the colorant, at the non-exposed areas. The colorant can be a dye or a pigment. Various types of pigments can be used such as organic pigments, inorganic pigments, carbon black, metallic powder pigments and fluorescent pigments. Organic pigments are preferred.

Specific examples of organic pigments include quinacridone pigments, quinacridonequinone pigments, dioxazine pigments, phthalocyanine pigments, anthrapyrimidine pigments, anthanthrone pigments, indanthrone pigments, flavanthrone pigments, perylene pigments, diketopyrrolopyrrole pigments, perinone pigments, quinophthalone pigments, anthraquinone pigments, thioindigo pigments, benzimidazolone pigments, isoindolinone pigments, azomethine pigments, and azo pigments.

Specific examples and more detailed information of pigments suitable as colorant in the current invention are described in EP 2 278 404 in paragraphs [0064] to [0068].

Typically, the amount of pigment in the coating may be in the range of about 0.005 $g/m^2$ to 2 $g/m^2$, preferably about 0.007 $g/m^2$ to 0.5 $g/m^2$, more preferably about 0.01 $g/m^2$ to 0.2 $g/m^2$, most preferably about 0.01 $g/m^2$ to 0.1 $g/m^2$.

The colorant can also be a dye. Any known dyes, such as commercially available dyes or dyes described in, for example, "Dye Handbook" (edited by the Organic Synthetic Chemistry Association, published in 1970) which are colored for the human eye, can be used as colorant in the photopolymerisable coating. Specific examples thereof are described in EP 2 278 404 in paragraph [0070].

Typically, the amount of dye in the coating may be in the range of about 0.005 $g/m^2$ to 2 $g/m^2$, preferably about 0.007 $g/m^2$ to 0.5 $g/m^2$, more preferably about 0.01 $g/m^2$ to 0.2 $g/m^2$, most preferably about 0.01 $g/m^2$ to 0.1 $g/m^2$.

The photopolymerisable layer or an optional other layer of the coating may include a printing-out agent, i.e. a compound which is capable of changing the color of the coating upon exposure. After image-wise exposing of the precursor, a visible image can be produced, hereinafter also referred to as "print-out image". The printing-out agent may be a compound as described in EP-A-1 491 356 paragraph [0116] to [0119] on page 19 and 20, and in US 2005/8971 paragraph [0168] to [0172] on page 17. Preferred printing-out agents are the compounds described in EP 1 765 592 from line 1 page 9 to line 27 page 20. More preferred are the IR-dyes as described in EP 1 736 312 from line 32 page 5 to line 9 page 32. The contrast of the image formed after image-wise exposure and processing is defined as the difference between the optical density at the exposed area to the optical density at the non-exposed area, and this contrast is preferably as high as possible. This enables the end-user to establish immediately whether or not the precursor has already been exposed and processed, to distinguish the different color selections and to inspect the quality of the image on the plate precursor. The contrast increases with increasing optical density in the exposed areas and/or decreasing optical density in the non-exposed areas. The optical density in the exposed area may increase with the amount and extinction coefficient of the colorant remaining in the exposed areas and the intensity of color formed by the printing-out agent. In the non-exposed areas it is preferred that the amount of colorant is as low as possible and that the intensity of color print-out agent is as low as possible. The optical density can be measured in reflectance using an optical densitometer, equipped with several filters (e.g. cyan, magenta, yellow). The difference in optical density in the exposed area and the non-exposed area has preferably a value of at least 0.3, more preferably at least 0.4, most preferably at least 0.5. There is no specific upper limit for the contrast value, but typically the contrast is not higher than 3.0 or even not higher than 2.0. In order to obtain a good visual contrast for a human observer the type of color of the colorant may also be important. Preferred colors for the colorant are cyan or blue colors, i.e. under blue color we understand a color that appears blue for the human eye.

The coating may include on the photopolymerisable layer, a toplayer or protective overcoat layer which acts as an oxygen barrier layer including water-soluble or water-swellable binders. Printing plate precursors which do not contain a toplayer or protective overcoat layer are also referred to as overcoat-free printing plate precursors. In the art, it is well-known that low molecular weight substances present in the air may deteriorate or even inhibit image formation and therefore usually a toplayer is applied to the coating. However, as a toplayer should be easily removable during development, adhere sufficiently to the photopolymerisable layer or optional other layers of the coating and should preferably not inhibit the transmission of light during exposure, overcoat-free photopolymer printing plate precursors are desirable. In the present invention, it has surprisingly been found that the overcoat-free printing plate precursor including the monomer including the moieties according to Formulae (I) and (VIII), or the monomers according to Formulae (IX), (X) or (XI) provide printing plates with excellent properties. Preferred binders which can be used in the toplayer are polyvinyl alcohol and the polymers disclosed in WO 2005/029190; U.S. Pat. No. 6,410,205 and EP 1 288 720, including the cited references in these patents and patent applications. The most preferred binder for the toplayer is polyvinylalcohol. The polyvinylalcohol has preferably a hydrolysis degree ranging between 74 mol % and 99 mol %, more preferably between 88-98%. The weight average molecular weight of the polyvinylalcohol can be measured by the viscosity of an aqueous solution, 4% by weight, at 20° C. as defined in DIN 53 015, and this viscosity number ranges preferably between 3 and 26, more preferably between 3 and 15, most preferably between 3 and 10.

The coating thickness of the optional toplayer is preferably between 0.25 and 1.75 g/m$^2$, more preferably between 0.25 and 1.3 g/m$^2$, most preferably between 0.25 and 1.0 g/m$^2$. In a more preferred embodiment of the present invention, the optional toplayer has a coating thickness between 0.25 and 1.75 g/m$^2$ and comprises a polyvinylalcohol having a hydrolysis degree ranging between 74 mol % and 99 mol % and a viscosity number as defined above ranging between 3 and 26.

The support is preferably a grained and anodized aluminium support, well known in the art. Suitable supports are for example disclosed in EP 1 843 203 (paragraphs [0066] to [0075]). The surface roughness, obtained after the graining step, is often expressed as arithmetical mean center-line roughness Ra (ISO 4287/1 or DIN 4762) and may vary between 0.05 and 1.5 µm. The aluminum substrate of the current invention has preferably an Ra value below 0.45 µm, more preferably below 0.40 µm and most preferably below 0.30 µm. The lower limit of the Ra value is preferably about 0.1 µm. More details concerning the preferred Ra values of the surface of the grained and anodized aluminum support are described in EP 1 356 926. By anodising the aluminum support, an $Al_2O_3$ layer is formed and the anodic weight (g/m$^2$ $Al_2O_3$ formed on the aluminum surface) varies between 1 and 8 g/m$^2$. The anodic weight is preferably ≥ 3 g/m$^2$, more preferably ≥ 3.5 g/m$^2$ and most preferably ≥ 4.0 g/m$^2$ The grained and anodized aluminium support may be subjected to so-called post-anodic treatments, for example a treatment with polyvinylphosphonic acid or derivatives thereof, a treatment with polyacrylic acid, a treatment with potassium fluorozirconate or a phosphate, a treatment with an alkali metal silicate, or combinations thereof. Alternatively, the support may be treated with an adhesion promoting compound such as those described in EP 1 788 434 in [0010] and in the non published patent application PCT/EP2013/055773. However, for a precursor optimized to be used without a pre-heat step it is preferred to use a grained and anodized aluminium support without any post-anodic treatment.

Besides an aluminium support, a plastic support, for example a polyester support, provided with one or more hydrophilic layers as disclosed in for example EP 1 025 992 may also be used.

The lithographic printing plate precursor of the present invention can be prepared by (i) applying on a support as described above the coating as described above and (ii) drying the precursor.

According to the present invention there is also provided a method for making a negative-working lithographic printing plate comprising the steps of imagewise exposing the printing plate precursor followed by developing the imagewise exposed precursor so that the non exposed areas are dissolved in the developer solution. Optionally, after the imaging step, a heating step is carried out to enhance or to speed-up the polymerization and/or crosslinking reaction.

The image-wise exposing step can be carried out by a laser. Preferably, the image-wise exposing step is carried out off-press in a platesetter, i.e. an exposure apparatus suitable for image-wise exposing the precursor with a laser such as a laser diode, emitting around 830 nm, a Nd YAG laser, emitting around 1060 nm, a violet laser, emitting around 400 nm, or a gas laser such as an Ar laser, or with a digitally modulated UV-exposure set-up, using e.g. digital mirror devices, or by a conventional exposure in contact with a mask. In a preferred embodiment of the present invention, the precursor is image-wise exposed by a laser emitting IR-light or violet light.

During the optional heating step the plate precursor is heated, preferably at a temperature of about 80° C. to 150° C. and preferably during a dwell time of about 5 seconds to 1 minute. The preheating step is preferably carried out in a preheating unit which is preferably provided with heating elements such as IR-lamps, UV-lamps, heated air, a heated metal roll, etc.

After the exposing step or, when a preheating step is present, after the preheating step, the precursor may be washed in a prewashing station, whereby at least part of the toplayer, if present, can be removed by supplying a wash liquid, i.e. water or an aqueous solution, to the coating of the precursor. The washing liquid is preferably water, more preferably tap water. More details concerning the wash step are described in EP 1 788 434 in [0026].

After the exposure step, the optional heating step and the optional prewashing step, the precursor is preferably developed by means of immersing the precursor in a developing solution. The developing step is preferably carried out off-press with an aqueous alkaline developing solution or a gum solution. During the development step, the non-exposed areas of the image-recording layer are at least partially removed without essentially removing the exposed areas. The processing liquid can be applied to the plate e.g. by rubbing with an impregnated pad, by dipping, immersing, (spin-)coating, spraying, pouring-on, either by hand or in an automatic processing apparatus. The treatment with a processing liquid may be combined with mechanical rubbing, e.g. by a rotating brush. The developed plate precursor can, if required, be post-treated with rinse water, a suitable correcting agent or preservative as known in the art. During the development step, any water-soluble protective layer present is preferably also removed. The development is preferably carried out at temperatures between 20 and 40° C. in automated processing units as customary in the art. More details concerning the development step can be found in for example EP 1 614 539 in [42] to [43]. Development in a gumming station comprising at least one gumming unit is for example described in WO 2007/057348 on page 40 line 34 to page 44 line 14.

The development step with an aqueous alkaline developing solution may be followed by a rinsing step and/or a gumming step.

Alternatively, the development step can be carried out by applying a gum solution thereby removing the non-exposed areas of the photopolymerisable layer from the support and gumming the plate in a single step. Preferably, the gumming unit is mechanically coupled to the platesetter by conveying means wherein the precursor is shielded from ambient light. A gum solution is typically an aqueous liquid which comprises one or more surface protective compounds that are capable of protecting the lithographic image of a printing plate against contamination, e.g. by oxidation, fingerprints, fats, oils or dust, or damaging, e.g. by scratches during handling of the plate. Suitable examples of such compounds are film-forming hydrophilic polymers or surfactants. The layer that remains on the plate after treatment with the gum solution preferably comprises between 0.005 and 20 g/m$^2$ of the surface protective compound, more preferably between 0.010 and 10 g/m$^2$, most preferably between 0.020 and 5 g/m$^2$. More details concerning the surface protective compounds in the gum solution can be found in WO 2007/057348 page 9 line 3 to page 11 line 6.

The gum solution preferably has a pH value between 3 and 11, more preferably between 4 and 10, even more preferably between 5 and 9, and most preferably between 6 and 8. A suitable gum solution is described in for example EP 1 342 568 in [0008] to [0022]. The viscosity of the gum solution can be adjusted to a value of e.g. between 1.7 and 5 mPa·s, by adding viscosity increasing compounds, such as poly(ethylene oxide) or polyvinylalcohol, e.g. having a molecular weight between 10$^4$ and 10$^7$. Such compounds can be present in a concentration of 0.01 to 10 g/l.

The gum solution may further comprise an inorganic salt, an anionic surfactant, a wetting agent, a chelate compound, an antiseptic compound, an anti-foaming compound and/or an ink receptivity agent and/or combinations thereof. More details about these additional ingredients are described in WO 2007/057348 page 11 line 22 to page 14 line 19.

Alternatively, the development step can be carried out on press by mounting the exposed precursor on a plate cylinder of a lithographic printing press and rotating the plate cylinder while feeding dampening liquid and/or ink to the coating.

After the processing step the plate may be dried in a drying unit. In a preferred embodiment the plate is dried by heating the plate in the drying unit which may contain at least one heating element selected from an IR-lamp, an UV-lamp, a heated metal roller or heated air. In a preferred embodiment of the present invention, the plate is dried with heated air as known in the drying section of a classical developing machine.

After drying the plate, the plate can optionally be heated in a baking unit. More details concerning the heating in a baking unit can be found in WO 2007/057348 page 44 line 26 to page 45 line 20.

The printing plate thus obtained can be used for conventional, so-called wet offset printing, in which ink and an aqueous dampening liquid is supplied to the plate. Another suitable printing method uses a so-called single-fluid ink without a dampening liquid. Suitable single-fluid inks have been described in U.S. Pat. Nos. 4,045,232; 4,981,517 and U.S. Pat. No. 6,140,392. In a most preferred embodiment, the single-fluid ink comprises an ink phase, also called the hydrophobic or oleophilic phase, and a polyol phase as described in WO 00/32705.

EXAMPLES

I. Compounds

| Compound | Commercial source | Structure |
|---|---|---|
| M-1 | Synthesis* | 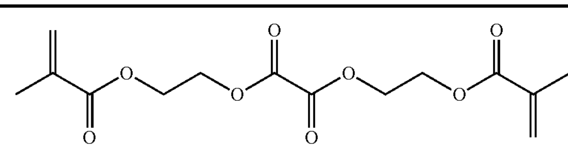 |
| M-2 | Synthesis* | 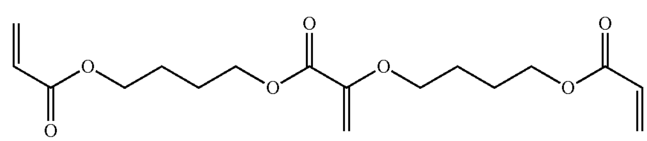 [SMILES: C=CC(=O)OCCCCOC(=C)C(=O)OCCCCOC(=O)C=C] |
| M-3 | Synthesis* | 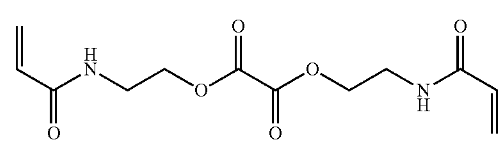 [SMILES: C=CC(=O)NCCOC(=O)C(=O)OCCNC(=O)C=C] |
| M-4 | Synthesis* | 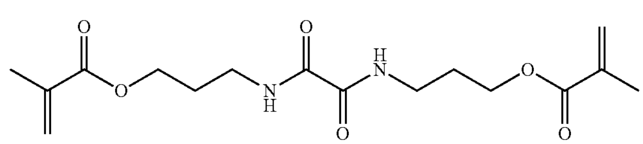 [SMILES: C=C(C)C(=O)OCCCNC(=O)C(=O)NCCCOC(=O)C(=C)C] |

-continued

| Compound | Commercial source | Structure |
|---|---|---|
| M-5** | FST510 commercially available from AZ ELECTRONICS MATERIALS | 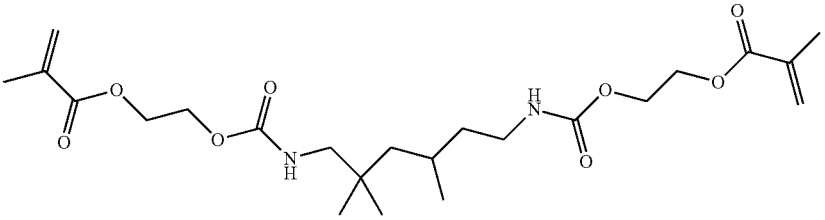 [SMILES: C=C(C)C(=O)OCCOC(=O)NCCC(C)CC(C)(C)CNC(=O)OCCOC(=O)C(=C)C] |
| M-6 | SR368 commercially available from SARTOMER | 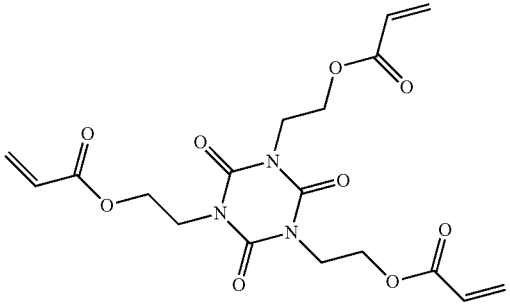 [SMILES: C=CC(=O)OCCn1c(=O)n(CCOC(=O)C=C)c(=O)n(CCOC(=O)C=C)c1=O] |
| M-7 | SR349 commercially available from SARTOMER | 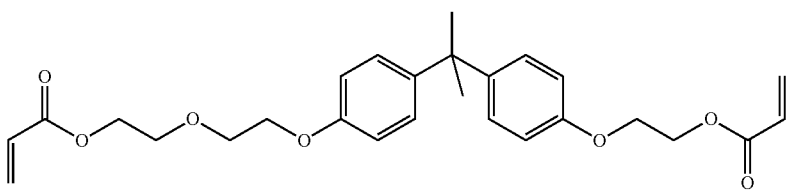 [SMILES: C=CC(=O)OCCOCCOc1ccc(C(C)(C)c2ccc(OCCOC(=O)C=C)cc2)cc1] |
| M-8 | SR259 commercially available from SARTOMER | 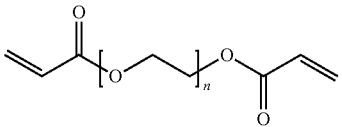<br>n = 4 on average |

*= see below
**= isomeric mixture

Synthesis of Inventive Compound M-1.

Reaction scheme:

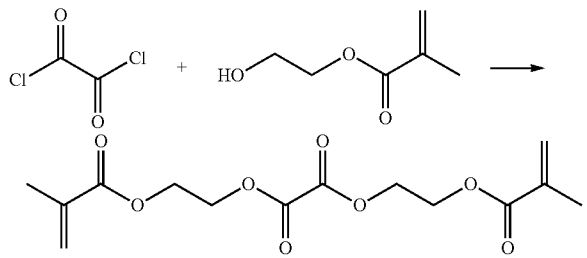

Experimental Procedure:

16.9 g hydroxyethyl methacrylate (Aldrich), 13.5 g triethylamine and 0.9 g 3,5-di-tert-butyl-4-hydroxytoluene were dissolved in 65 ml dichloromethane at room temperature and the solution was cooled to −10° C. A solution of 8.3 g oxalyl chloride in 35 ml dichloromethane was cooled to −10° C. and added dropwise to the reaction mixture. The reaction mixture was stirred for 1 hour at 0° C. and successively 3 hours at room temperature. The reaction mixture was poured on 200 g ice and stirred for 1 hour. The product was extracted with 200 ml dichloromethane. The organic phase was washed with a 1 molar aqueous HCl solution, a saturated aqueous NaHCO₃ solution and a saturated aqueous NaCl solution. Successively, the organic phase was dried with MgSO₄ and evaporated under reduced pressure. The product was purified by recrystallized from methyl-t-butyl ether with n-hexane. The product was analyzed using TLC-chromatography (TLC Silica gel 60 F254; supplied by Merck, eluent: methylene chloride/ethyl acetate 90/10, Rf: 0.61).

Synthesis of Inventive Compound M-2.

Reaction scheme:

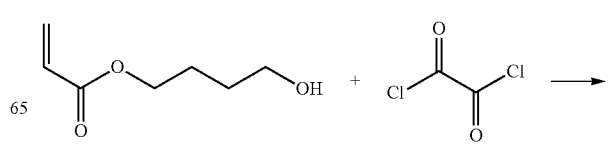

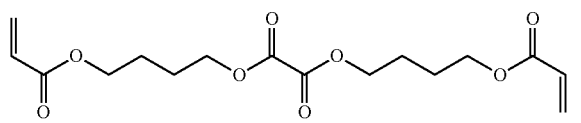

5

Experimental Procedure:

57.7 g 4-hydroxybutyl methacrylate (Nippon Kasei Chemical Company Limited), 41.7 g triethylamine and 2.6 g 3,5-di-tert-butyl-4-hydroxytoluene were dissolved in 270 ml dichloromethane at room temperature and the solution was cooled to −10° C. A solution of 25.4 g oxalyl chloride in 150 ml dichloromethane was cooled to −10° C. and added dropwise to the reaction mixture. The reaction mixture was stirred for 30 minutes at 0° C. and successively over night at room temperature. The reaction mixture was poured on 660 g ice and stirred for 1 hour. The product was extracted with 250 ml dichloromethane. The organic phase was washed with a 1 molar aqueous HCl solution, a saturated aqueous NaHCO3 solution and a saturated aqueous NaCl solution. Successively, the organic phase was dried with $MgSO_4$ and evaporated under reduced pressure. The product was purified by column chromatography using a Prochrom LC80 column, packed with Kromasil Si 60 å 10 μm and methylene chloride/ethyl acetate 90/10 as eluent. The compound was analyzed using TLC-chromatography (TLC Silica gel 60 $F_{254}$; supplied by Merck, eluent: methylene chloride/ethyl acetate 96/4, $R_f$: 0.3).

Synthesis of Inventive Compound M-3.

Reaction scheme:

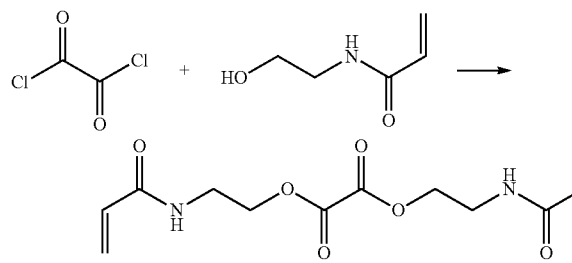

Experimental Procedure:

7.1 g N-hydroxyethyl acrylamide (Aldrich), 6.25 g triethylamine and 0.39 g 3,5-di-tert-butyl-4-hydroxytoluene were dissolved in 33 ml isopropyl acetate at room temperature and the solution was cooled to −5° C. A solution of 4.2 g oxalyl chloride in 23 ml isopropyl acetate was cooled to −5° C. and added dropwise to the reaction mixture. The reaction mixture was stirred for 1 hour at −5° C. and successively 2 hours at room temperature. The product precipitated in the reaction mixture as a white powder and was filtrated and washed with isopropyl acetate. The product was washed at 5° C. with a 3 molar aqueous NaCl solution in order to remove salts. The product was successively filtered and dissolved in methylene chloride/methanol 60/40 volume %. The mixture was filtered and the filtrate was evaporated under reduced pressure. The product was obtained as a white powder. The compound was analyzed using TLC-chromatography (TLC Silica gel 60 F254; supplied by Merck, eluent: methylene chloride/methanol 92/2, Rf: 0.3).

Synthesis of Comparative Compound M-4.

1. Synthesis of N,N'-Bis(3-hydroxypropyl)oxamide

Reaction scheme:

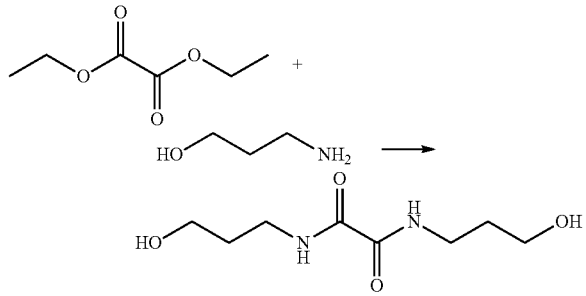

Experimental Procedure:

1 g diethyl oxalate (99% from ACROS) was dissolved in 5 ml ethanol. 1.03g 3-amino-1-propanol (99% from ACROS) was added dropwise to the solution. The mixture was stirred for 1 hour at room temperature. The product (white precipitate) was filtrated, washed with ethanol and dried. The compound was analyzed using TLC-chromatography (TLC Silica gel 60 $F_{254}$; supplied by Merck, eluent: methylene chloride/methanol 90/10, $R_f$: 0.15).

2. Synthesis of M-4

Reaction scheme:

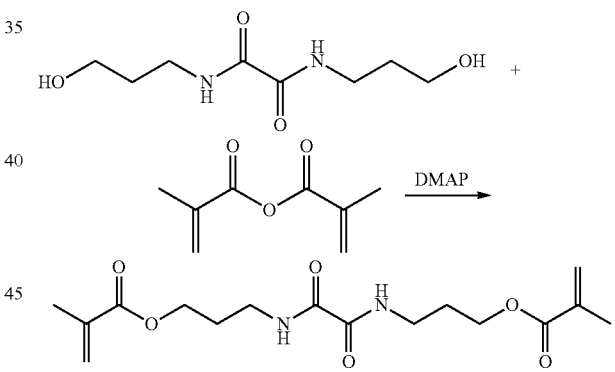

Experimental Procedure:

1 g N,N'-Bis(3-hydroxypropyl)oxamide was added to 10 ml of dichloromethane. 4.1 ml triethylamine and 0.006g 4-dimethylaminopyridine were added to the mixture. 2.26 g methacrilic anhydride (>94% from ALDRICH) was added dropwise to the mixture. The reaction was allowed to continue over night at room temperature under mild stirring. The reaction mixture was evaporated under reduced pressure. The product was purified by column chromatography using a GraceResolve RS80 column from Grace, packed with 35-45 μm silica and methylene chloride as solvent. The compound was analyzed using TLC-chromatography (TLC Silica gel 60 $F_{254}$; supplied by Merck, eluent: methylene chloride/methanol 90/10, $R_f$: 0.80).

II. Example 1

Solubility of the Compounds 100 mg of the inventive and comparative compounds were added to 5 ml of a CertiPUR pH=7 buffer solution available from Merck. The mixture was gently stirred at room temperature and the homogeneity of the mixture was evaluated visually after different times:

TABLE 1

Visual homogeneity of a mixture of 100 mg compound in a 5 ml aqueous buffer pH = 7

| Compound | Visual homogeneity | | | | |
|---|---|---|---|---|---|
| | After 1 hour | After 1 day | After 4 days | After 1 week | After 2 weeks |
| M-1 inventive | − | − | − | + | + |
| M-2 inventive | − | − | − | + | + |
| M-3 inventive | − | + | + | + | + |
| M-4 comparative | − | − | − | − | − |
| M-5 comparative | − | − | − | − | − |
| M-6 comparative | − | − | − | − | − |
| M-7 comparative | − | − | − | − | − |
| M-8 comparative | − | − | − | − | − |

− = heterogeneous mixture
+ = homogeneous mixture

The results in Table 1 indicate that the mixtures containing the inventive compounds M-1 and M-2 become homogeneous after 1 week, while the mixtures with the comparative compounds remain heterogeneous. The mixture containing the inventive compound M-3 becomes homogeneous already after 1 day. Without being limited to any theoretical explanation and/or hypothesis, it is believed that the inventive compounds M-1, M-2 and M-3 hydrolyse in the aqueous environment and form soluble products in the developer; especially the solution containing compound M-3 including an oxalate ester and an acrylamide group.

III. Example: 2 Violet Photopolymer Printing Plates.
I. Preparation of the Printing Plates PP-01 to PP-16
Preparation of the Aluminium Support S-01

A 0.3 mm thick aluminium foil was degreased by spraying with an aqueous solution containing 26 g/l NaOH at 65° C. for 2 seconds and rinsed with demineralised water for 1.5 seconds. The foil was then electrochemically grained during 10 seconds using an alternating current in an aqueous solution containing 15 g/l HCl, 15 g/l $SO_4^{2-}$ ions and 5 g/l $Al^{3+}$ ions at a temperature of 37° C. and a current density of about 100 A/dm². Afterwards, the aluminium foil was then desmutted by etching with an aqueous solution containing 5.5 g/l of NaOH at 36° C. for 2 seconds and rinsed with demineralised water for 2 seconds. The foil was subsequently subjected to anodic oxidation during 15 seconds in an aqueous solution containing 145 g/l of sulfuric acid at a temperature of 50° C. and a current density of 17 A/dm², then washed with demineralised water for 11 seconds and dried at 120° C. for 5 seconds.

The support thus obtained was characterized by a surface roughness Ra of 0.35-0.4 μm (measured with interferometer NT1100) and had an anodic weight of 3.0 g/m².

Coating
Photopolymerisable Layer PL-01

The printing plate precursors were produced by coating onto the above described support S-01 the components as defined in Table 2 dissolved in a mixture of 40% by volume of MEK and 60% by volume of Dowanol PM (1-methoxy-2-propanol, commercially available from DOW CHEMICAL Company). The coating solution was applied at a wet coating thickness of 30 μm and then dried at 120° C. for 1 minute in a circulation oven.

TABLE 2 dry coating weight of the photopolymerisable layer PL-01.

| INGREDIENTS* PL-01 | g/m² |
|---|---|
| Fluomix (1) | 0.075 |
| Poly(vinyl acetate) (2) | 0.225 |
| Monomer (3) | 0.900 |
| Tegoglide 410 (4) | 0.0023 |
| HABI (5) | 0.1125 |
| Hostaperm Blue P-BFSTM (6) | 0.090 |
| Disperbyk 182 (7) | 0.090 |
| MBT (8) | 0.030 |
| Albritect CP30 (9) | 0.036 |
| Sipomer PAM100 (10) | 0.195 |
| Dry coating weight | 1.1756 |

*active ingredients in the coating (1) Fluomix is a violet sensitizer mixture consisting of the following compounds:

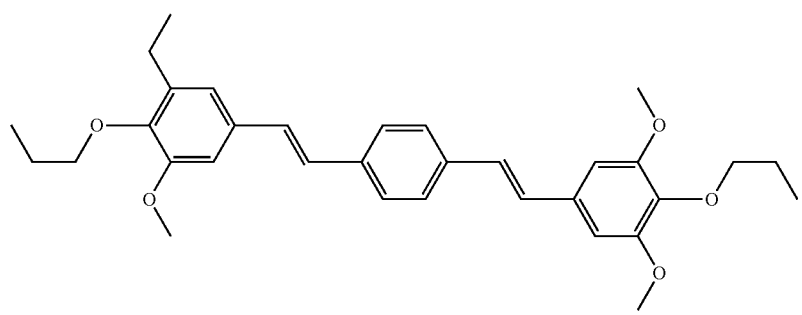

15 wt. %

-continued

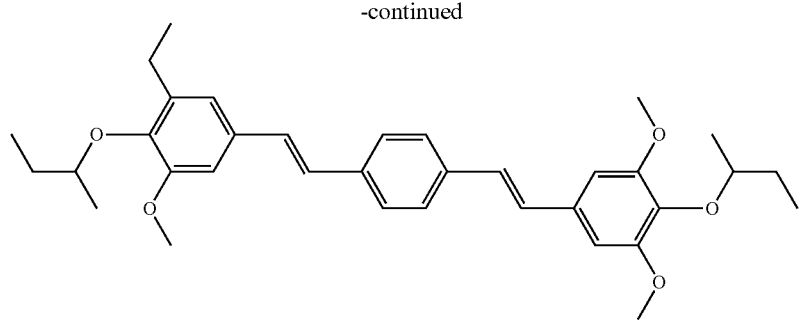

38 wt. %

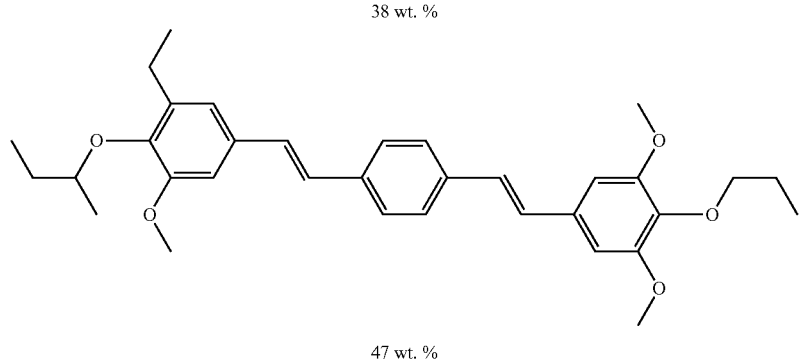

47 wt. %

(2) Poly(vinyl acetate) with Mw=500.000 commercially available from ALDRICH;

(3) Monomer combinations as defined in Tables 4 and 5 below;

(4) Tegoglide 410TM is a surfactant commercially available from Evonik Tego Chemie GmbH;

(5) HABI is 2,2'-bis(o-chlorophenyl)-4,4',5,5'-tetraphenylbiimidazole commercially available from SUMITOMO;

(6) and (7) Hostaperm Blue P-BFSTM commercially available from Clariant and Disperbyk 182 commercially available from BYK Chemie GmbH. were added to the coating solution as a dispersion: Hostaperm Blue P-BFSTM 15 mass % and Disperbyk 182 15 mass % in Dowanol PM (1-methoxy-2-propanol, commercially available from DOW CHEMICAL Company);

(8) MBT is 2-mercaptobenzthiazole;

(9) Albritect CP30 is a poly(acrylic acid) poly(vinylphosphonic acid) 70/30 copolymer from RHODIA;

(10) Sipomer PAM100 is a phosphate esters of polyethylene glycol monomethacrylate from RHODIA.

Top Layer OC-1

Optionally on top of the photosensitive layer a solution in water with the composition as defined in Table 3 was coated (40 μm) and dried at 120° C. for 2 minutes. The so-formed protective top layer OC-1 has a dry thickness or dry coating weight of 1.25 g/m². The presence/absence of a top layer OC-1 is defined in Tables 4 and 5.

TABLE 3

Composition of the top layer solution OC-01.

| INGREDIENTS OC-01 | g |
|---|---|
| Moil 4-88 (1) | 19.1 |
| Mowiol 8-88 (1) | 5.84 |
| Luviskol K30 (2) | 5.95 |
| Acticide LA1206 (3) | 0.06 |
| Lutensol A8 (4) | 0.30 |
| Water | 969 |

(1) Mowiol 4-88 ™ and Mowiol 8-88 ™ are partially hydrolyzed polyvinylalcohols commercially available from Kuraray;
(2) Luviskol K30 ™ is polyvinylpyrrolidone homopolymer commercially available from BASF;
(3) Acticide LA1206 ™ is a biocide commercially available from Thor;
(4) Lutensol A8 ™ is a surface active agent commercially available from BASF.

Imaging

The printing plate precursors were subsequently imaged with a Polaris VXT platesetter at 1270 dpi (110 1pi Agfa Balanced Screening (ABS))(both commercially available from Agfa Graphics NV and equipped with a 405 nm violet laser diode) and this at energy densities between 128 and 142 μJ/cm².

The sensitivity, i.e. right exposure, was determined for each printing plate precursor using an Agfa Polaris VXT platesetter at 1270 dpi through an UGRA Step Wedge (wedge constant of 0.15). The sensitivity is defined as the exposure energy density (in μJ/cm²) needed to obtain an optical density >97% of the maximum optical density that can be obtained on this plate after processing on the first three wedge steps. The obtained sensitivity results are given in Tables 4 and 5.

Processing

After imaging, the printing plate precursors were subjected to processing with a VIOLET CF GUM-NP™ commercially available from Agfa Graphics NV in a CRF45 processor™ (dwell time 30 s, at 21° C.), available from Agfa Graphics, to remove the coating in the non-image areas from the support.

II. Artificial Ageing of the Printing Plates

The obtained printing plates were cut into two parts. The first part is further referred to as the "fresh" printing plate. The second part was artificially aged by storing it during 5 days in a cabinet conditioned at 34° C. and 80% R.H. This second part is further referred to as the "aged" printing plate. After ageing the "aged" printing plate was allowed to cool down to room temperature before printing. Printing plates PP-01 to PP-16 were obtained.

Results

Evaluation of the Ink Acceptance on Press:

The "fresh" and "aged" printing plates PP-01 to PP-16 were mounted on a Heidelberg GTO 46 printing press (available form Heidelberger Druckmaschinen AG). Each print job was started using K+E Novavit 800 Skinnex ink (trademark of BASF Druckfarben GmbH)and 2 wt % Prima FS404 (trademark of Agfa Graphics) in water as fountain solution. A compressible blanket ContiAir Entropia HC (trademark of Continental GmbH) was used and printing was performed on non-coated offset paper. The ink acceptance on press was examined by visual inspection on the plate after printing of 50 pages (see Tables 4 and 5).

TABLE 4

Ink acceptance on press of the printing plates provided with an overcoat layer.

| Printing plate | Ageing | Imaging Energy (μJ/cm$^2$) | Sensitivity (μJ/cm$^2$) | Monomer composition * (mg/cm$^2$) | Ink acceptance |
|---|---|---|---|---|---|
| PP-01 comparative | fresh | 128 | 96 | M-5 (900) | yes |
| PP-02 comparative | aged | 128 | 88 | M-5 (900) | yes |
| PP-03 comparative | fresh | 127 | 127 | M-7 (450) and M-5 (450) | yes |
| PP-04 comparative | aged | 127 | 127 | M-7 (450) and M-5 (450) | yes |
| PP-05 inventive | fresh | 142 | 247 | M-5 (360) + M-4 (180) + M-2 (360) | yes |
| PP-6 inventive | aged | 142 | 247 | M-5 (360) + M-4 (180) + M-2 (360) | yes |
| PP-7 inventive | fresh | 142 | 187 | M-5 (360) + M-4 (180) + M-1 (360) | yes |
| PP-8 inventive | aged | 142 | 126 | M-5 (360) + M-4 (180) + M-1 (360) | yes |
| PP-9 inventive | fresh | 50 | 50 | M-5 (450) + M-3 (450) | yes |
| PP-10 inventive | aged | 50 | 50 | M-5 (450) + M-3 (450) | yes |

* M-1 to M-5 see above

TABLE 5

Ink acceptance on press of the printing plates without overcoat layer.

| Printing plate | Ageing | Imaging Energy (μJ/cm$^2$) | Sensitivity (μJ/cm$^2$) | Monomer composition* (mg/cm$^2$) | Ink acceptance |
|---|---|---|---|---|---|
| PP-11 inventive | fresh | ** | ** | M-5 (450) + M-1 (450) | — |
| PP-12 inventive | Aged | ** | ** | M-5 (450) + M-1 (450) | — |
| PP-13 inventive | fresh | ** | ** | M-5 (450) + M-2 (450) | — |
| PP-14 inventive | aged | ** | ** | M-5 (450) + M-2 (450) | — |
| PP-15 inventive | fresh | 93 | 93 | M-5 (450) + M-3 (450) | yes |
| PP-16 inventive | aged | 93 | 93 | M-5 (450) + M-3 (450) | yes |

*M-1, M-2, M-3 and M-5 see above;
** no image formation

The results in Tables 4 and 5 show that all the printing plates containing an overcoat—including the printing plates which were aged during 5 days at 34° C. and 80% R.H.—result in a good ink acceptance on press;

the overcoat-free printing plates PP-15 and PP-16 comprising the hydrolysable compound including an oxalate ester combined with an acrylamide group result in a good ink acceptance on press.

As the printing plates containing the hydrolysable compounds according to the present invention M-1, M-2 and M-3 result in a good ink acceptance on press, it is believed that, although M-1, M-2 and M-3 most probably hydrolyse in the aqueous developer solution, (pH=7, see Table 1, Example 1), these compounds do not significantly hydrolyse in the photopolymerisable layer. Indeed, it is believed that hydrolysis of the compounds M-1, M-2 and M-3 in the photopolymerisable layer would render the coating hydrophilic resulting in a bad ink acceptance.

The results in Tables 4 and 5 further show that the inventive printing plates PP-09 to PP-10 including inventive compound M-3 (monomer including an oxalate ester combined with an acrylamide group) have a significant improved sensitivity, even without an overcoat layer (PP-15 and PP-16), compared to the other printing plates.

III. Exhaustion Behaviour of the Gum Developer Solution.

The effect of plate composition on the gum developer properties were investigated with VIOLET CF GUM-NP™ commercially available from Agfa Graphics NV in a small scale dip tank processor having 1 brush for supporting layer removal. Brush speed was at 120 rpm applying a brush pressure between 300 and 400 g. Additionally the following processor parameters were used:

800 ml filling volume
24+/−1° C. bath temperature
1.0 m/min. transportation speed
(equal to a bath dwell time of 17 s and a soak time of 8 s before brush)
16 m$^2$ was used for saturation (=20 m$^2$/l developer) of the inventive printing plate PP-A and comparative printing plate PP-B.

The printing plates PP-A and PP-B were produced following the procedures as described above. Onto the above described support S-01 the components as defined in Table 2 (see above) including respectively monomer M-1 (PP-A) and monomer M-5 (PP-B) were coated. Subsequently, the protective top layer OC-1 was applied. After imaging and processing the printing plates PP-A and PP-B were obtained.

The mass of sediment (sludge) obtained after 7 days of storage was determined gravimetrically by centrifugation of the developing solutions(45 min/4000 rpm/25 ° C.) under a dedicated time schedule (0, 1, 3, 5 and 7 days). After separation the solid phase was dried over 3 h at 110° C. From these weights, mean values were calculated and the average sludge (g/kg) was obtained. Also, the morphology of the loaded gum solutions at the day of saturation was evaluated by transmission light microscopy at 100 fold enlargement by spreading 1 drop gum solution on a flat glass sample substrate. Finally, a visual comparison of the appearance of the processor was done after draining and water rinse. The results are summarized in Table 6 shown in the FIGURE.

The results in Table 6 show that the printing plate including the compound according to the present invention results in a significant lower formation of sludge in the gum developer (average sludge) as also visualized by the obtained morphology of the gum developer by microscope; and a more clean processor after draining and/or rinsing with water compared to the printing plate including the comparative compound.

IV. Example 3: Thermal Photopolymer Printing Plates.
I. Preparation of the Printing Plates PP-17 to PP-22
Coating
Photopolymerizable layer PL-02

The printing plate precursors were produced by coating onto the above described support S-01 the components as defined in Table 7 dissolved in a mixture of 40% by volume of MEK and 60% by volume of Dowanol PM (1-methoxy-2-propanol, commercially available from DOW CHEMICAL Company). The coating solution was applied at a wet coating thickness of 30 μm and then dried at 120° C. for 1 minute in a circulation oven.

TABLE 7

Composition and dry coating weight of the photopolymerisable layer PL-02.

| INGREDIENTS* PL-02 | g/m$^2$ |
|---|---|
| IR dye (1) | 0.033 |
| Poly(vinyl acetate) (2) | 0.225 |
| Monomer (3) | 0.900 |
| Tegoglide 410 (4) | 0.0023 |
| Tetraphenylborate (5) | 0.090 |
| Pig-disp-01 (6) | 0.180 |
| Albritect CP30 (7) | 0.036 |
| Sipomer PAM100 (8) | 0.195 |
| Dry coating weight | 1.756 |

*active ingredients in the coating
(1) IR dye is an infrared absorbing dye having the following structure:

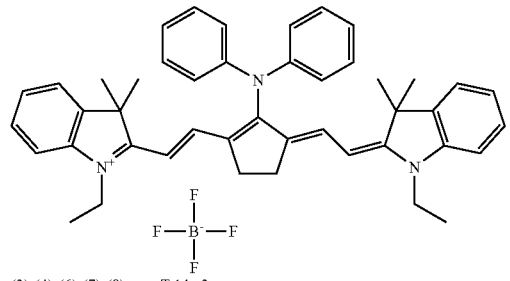

(2) (4) (6) (7) (8): see Table 2;
(3) monomer combinations as defined in Table 8 below;
(5) Bis (4-tert-butylphenyl) iodonium tetraphenylborate commercially available from HAMPFORD RESEARCH.

Top Layer OC-1

On top of the photosensitive layer, a solution in water with the composition as defined in Table 3 was coated (40 μm) and dried at 120° C. for 2 minutes. The so-formed protective top layer OC-1 has a dry thickness or dry coating weight of 1.25 g/m$^2$.

Imaging

The printing plate precursors were subsequently imaged at 2400 dpi with a Creo 3244T thermal platesetter™ (200 lpi Agfa Balanced Screening (ABS)), commercially available from Kodak and equipped with a 830 nm IR laser diode, at energy densities of 90 mJ/cm$^2$.

Processing

After imaging, the printing plate precursors were subjected to processing with a VIOLET CF GUM-NP commercially available from Agfa Graphics NV in a CRF45 processor (dwell time 30 s, at 21° C.), commercially available from Agfa Graphics, to remove the coating in the non-image areas from the support.

II. Artificial ageing of the Printing plates PP-17 to PP-22.

The obtained printing plates were cut into two parts. The first part is further referred to as the "fresh" printing plate. The second part was artificially aged by storing it during 5 days in a cabinet conditioned at 34° C. and 80% R.H. This second part is further referred to as the "aged" printing plate. After ageing the "aged" printing plate was allowed to cool down to room temperature before printing. The printing plates PP-17 to PP-22 were obtained.

Results
Evaluation of the Ink Acceptance on Press:

The "fresh" and "aged" printing plates PP-17 to PP-22 were mounted on a Heidelberg GTO 46 printing press (available form Heidelberg). Each print job was started using K+E Novavit 800 Skinnex ink (trademark of BASF Druckfarben GmbH)and 2 wt % Prima FS404 (trademark of Agfa Graphics) in water as fountain solution. A compressible blanket ContiAir Entropia HC (trademark of Continental GmbH) was used and printing was performed on non-coated offset paper. The ink acceptance on press was examined by visual inspection on the plate after printing 50 pages (see Table 8).

TABLE 8

Ink acceptance on press of the printing plates.

| Printing plate | Ageing | Monomer (mg/cm$^2$) | Ink acceptance |
|---|---|---|---|
| PP-17 comparative | fresh | M-4 (900) | Yes |
| PP-18 comparative | aged | M-4 (900) | Yes |
| PP-19 Inventive | fresh | M-4 (450) + M-1 (450) | Yes |
| PP-20 inventive | aged | M-4 (450) + M-1 (450) | Yes |
| PP-21 inventive | fresh | M-4 (450) + M-2 (450) | Yes |
| PP-22 inventive | aged | M-4 (450) + M-2 (450) | Yes |

The results in Table 8 show that all the Examples result in a good ink acceptance on press, including the printing plates which were aged during 5 days at 34° C. and 80% R.H. As the Examples with the inventive compounds M-1 and M-2 result in a good ink acceptance on press, it is believed that, although the inventive compounds M-1 and M-2 most probably hydrolyse in the aqueous developer solution (pH =7, see Table 1, Example 1), these compounds do not significantly hydrolyse in the photopolymerisable layer. Indeed, it is believed that hydrolysis of the compounds M-1 and M-2 in the photopolymerisable layer would render the coating hydrophilic resulting in a bad ink acceptance.

The invention claimed is:

1. A lithographic printing plate precursor comprising:
a support including a hydrophilic surface or a hydrophilic layer; and
a coating including a photopolymerizable layer; wherein the photopolymerizable layer includes a compound including a free radical polymerizable group and at least one moiety having a structure according to Formula (I):

$$*-O-\underset{O}{\underset{\|}{C}}-\underset{O}{\underset{\|}{C}}-X-*$$

wherein
X represents O; and
* denotes linking positions to remaining portions of the compound.

2. The lithographic printing plate precursor according to claim 1, wherein the compound is represented by Formula (II):

$$\left[A^1\right]_a-L^1-O-\underset{O}{\underset{\|}{C}}-\underset{O}{\underset{\|}{C}}-X-\left[L^*-X-\underset{O}{\underset{\|}{C}}-\underset{O}{\underset{\|}{C}}-O-\right]_c L^2-\left[A^2\right]_b$$

wherein
X represents O;
$L^1$ and $L^2$ are independently a divalent, trivalent, four-valent, five-valent, or six-valent linking group;
L* represents a divalent linking group;
$A^1$ and $A^2$ independently represent an ethylenical unsaturated group or a terminal group;
a represents 1, 2, 3, 4, or 5, respectively, for the divalent, trivalent, four-valent, five-valent, or six-valent linking group $L^1$;
b represents 1, 2, 3, 4, or 5, respectively, for the divalent, trivalent, four-valent, five-valent, or six-valent linking group $L^2$; and
c is an integer ranging from 0 to 150.

3. The lithographic printing plate precursor according to claim 2, wherein the compound is represented by Formula (V):

$$\left[A^1\right]_a-L^1-O-\underset{O}{\underset{\|}{C}}-\underset{}{\overset{O}{\|}}-X-L^2-\left[A^2\right]_b$$

wherein
X represents O;
$L^1$ and $L^2$ are independently a divalent, trivalent, four-valent, five-valent, or six-valent linking group;
$A^1$ and $A^2$ independently represent an ethylenical unsaturated group or a terminal group;
a represents 1, 2, 3, 4, or 5, respectively, for the divalent, trivalent, four-valent, five-valent, or six-valent linking group $L^1$; and
b represents 1, 2, 3, 4, or 5, respectively, for the divalent, trivalent, four-valent, five-valent, or six-valent linking group $L^2$.

4. The lithographic printing plate precursor according to claim 3, wherein the compound is represented by Formula (VI):

$$A^1-L^1-O-\underset{O}{\underset{\|}{C}}-\underset{}{\overset{O}{\|}}-X-L^2-A^2$$

wherein
X represents O;
$L^1$ and $L^2$ represent a divalent linking group; and
$A^1$ and $A^2$ independently represent an ethylenical unsaturated group or a terminal group.

5. The lithographic printing plate precursor according to claim 2, wherein the ethylenical unsaturated group includes an acrylamide group or a methacrylamide group.

6. The lithographic printing plate precursor according to claim 3, wherein the ethylenical unsaturated group includes an acrylamide group or a methacrylamide group.

7. The lithographic printing plate precursor according to claim 4, wherein the ethylenical unsaturated group includes an acrylamide group or a methacrylamide group.

8. The lithographic printing plate precursor according to claim 2, wherein $L^1$ and $L^2$ independently represent an optionally substituted alkylene, cycloalkylene, arylene, or heteroarylene, —CH2-, —O—, —CO—, —CO—O—, —O—CO—, —CO—NH—, —NH—CO—, >N—CO—, —CO—N<, —NH—CO—O—, >N—CO—O—, —O—CO—NH—, —O—CO—N<, —NH—CO—NH—, >N—CO—NH—, —NH—CO—N<, >N—CO—N<, —NH—CS—NH—, >N—CS—NH—, —NH—CS—N<, >N—CS—N<, —CO—NR'—, —NR"—CO—, —SO—, —SO₂—, —SO₂—NH—, —SO₂—N<, —NH—SO₂—, >N—SO₂—, —CH=N—, >C=N—, —NH—NH—, >N—NH—, —NH—N<, >N—N<, —N⁺(CH₃)₂—, —N⁺(CH₃)<, >N⁺(CH₃)—, >N⁺<, —S—, —S—S—, —NH—CO—CO—NH—, —NH—CO—CO—N<, >H—CO—CO—NH—, >N—CO—CO—N<, $$-\underset{H_2}{C}-\underset{|}{\overset{CH_2}{\underset{|}{C}}}-\underset{H_2}{C}-O-\underset{H_2}{C}-\underset{|}{\overset{CH_2}{\underset{|}{C}}}-\underset{H_2}{C}-$$

and/or combinations thereof; and
R' and R" each independently represent an optionally substituted alkyl, aryl, aralkyl, or heteroaryl.

9. The lithographic printing plate precursor according to claim 3, wherein $L^1$ and $L^2$ independently represent an optionally substituted alkylene, cycloalkylene, arylene, or heteroarylene, —CH2-, —O —, —CO—, —CO—O—, —O—CO—, —CO—NH—, —NH—CO—, >N—CO—, —CO—N<, —NH—CO—O—, >N—CO—O—, —O—CO—NH—, —O—CO—N<, —NH—CO—NH—, >N—CO—NH—, —NH—CO—N<, >N—CO—N<, —NH—CS—NH—, >N—CS—NH—, —NH—CS—N<, >N—CS—N<, —CO—NR'—, —NR"—CO—, —SO—, —SO$_2$—, —SO$_2$—NH—, —SO$_2$—N<, —NH—SO$_2$—, >N—SO$_2$—, —CH=N—, >C=N—, —NH—NH—, >N—NH—, —NH—N<, >N—N<, —N$^+$(CH$_3$)$_2$—, —N$^+$(CH$_3$)<, >N$_+$(CH$_3$)—, >N$^+$<, —S—, —S—S—, —NH—CO—CO—NH—, —NH—CO—CO—N<, >H—CO—CO—NH—, >N—CO—CO—N<,

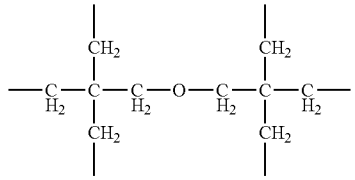 [SMILES: CCC(CC)(CC)COCC(CC)(CC)CC]

and/or combinations thereof; and

R' and R" each independently represent an optionally substituted alkyl, aryl, aralkyl, or heteroaryl.

10. The lithographic printing plate precursor according to claim 4, wherein $L^1$ and $L^2$ independently represent an optionally substituted alkylene, cycloalkylene, arylene, or heteroarylene, —CH2-, —O—, —CO—, —CO—O—, —O—CO—, —CO—NH—, —NH—CO—, >N—CO—, —CO—N<, —NH—CO—O—, >N—CO—O—, —O—CO—NH—, —O—CO—N<, —NH—CO—NH—, >N—CO—NH—, —NH—CO—N<, >N—CO—N<, —NH—CS—NH—, >N—CS—NH—, —NH—CS—N<, >N—CS—N<, —CO—NR'—, —NR"—CO—, —SO—, —SO$_2$—, —SO$_2$—NH—, —SO$_2$—N<, —NH—SO$_2$—, >N—SO$_2$—, —CH=N—, >C=N—, —NH—NH—, >N—NH—, —NH—N<, >N—N<, —N$^+$(CH$_3$)$_2$—, —N$^+$(CH$_3$)<, >N$^+$(CH$_3$)—, >N$^+$<, —S—, —S—S—, —NH—CO—CO—NH—, —NH—CO—CO—N<, >H—CO—CO—NH—, >N—CO—CO—N<,

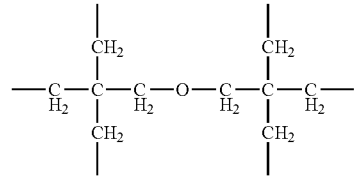

and/or combinations thereof; and

R' and R" each independently represent an optionally substituted alkyl, aryl, aralkyl, or heteroaryl.

11. A method of making the lithographic printing plate precursor according to claim 1, the method comprising the steps of:

providing the support and the coating ;
applying the coating to the support; and
drying the lithographic printing plate precursor.

12. A method of making a lithographic printing plate comprising the steps of:

providing the lithographic printing plate precursor according to claim 1;
image-wise exposing the lithographic printing plate precursor with a laser emitting IR-light or violet light; and
developing the lithographic printing plate precursor off-press by treating the lithographic printing plate precursor with a developing solution to remove non-exposed areas of the coating from the support.

* * * * *